US011485231B2

(12) United States Patent
Winton et al.

(10) Patent No.: US 11,485,231 B2
(45) Date of Patent: Nov. 1, 2022

(54) SYSTEMS AND METHODS FOR PROVIDING NATURE SOUNDS

(71) Applicant: Harman International Industries, Incorporated, Stamford, CT (US)

(72) Inventors: Riley Winton, Opelika, AL (US); Christopher Michael Trestain, Livonia, MI (US); Maxwell Willis, Royal Oak, MI (US); Chris Ludwig, Bloomfield Hills, MI (US)

(73) Assignee: Harman International Industries, Incorporated, Stamford, CT (US)

( * ) Notice: Subject to any disclaimer, the term of this patent is extended or adjusted under 35 U.S.C. 154(b) by 13 days.

(21) Appl. No.: 17/112,684

(22) Filed: Dec. 4, 2020

(65) Prior Publication Data
US 2021/0197667 A1 Jul. 1, 2021

Related U.S. Application Data

(60) Provisional application No. 63/026,621, filed on May 18, 2020, provisional application No. 62/954,195, filed on Dec. 27, 2019.

(51) Int. Cl.
*B60K 35/00* (2006.01)
*B60W 50/14* (2020.01)

(52) U.S. Cl.
CPC ............ *B60K 35/00* (2013.01); *B60W 50/14* (2013.01); *B60K 2370/157* (2019.05); *B60K 2370/48* (2019.05); *B60W 2050/146* (2013.01); *B60W 2400/00* (2013.01)

(58) Field of Classification Search
None
See application file for complete search history.

(56) References Cited

U.S. PATENT DOCUMENTS

| 10,638,248 B1 * | 4/2020 | Dodds .............. G10K 11/17873 |
| 2002/0154179 A1 * | 10/2002 | Wilcock .............. G11B 19/025 |
| 2008/0215239 A1 * | 9/2008 | Lee .................... G01C 21/3629 701/441 |

(Continued)

FOREIGN PATENT DOCUMENTS

| CN | 106664473 A * | 5/2017 | .......... G10K 11/178 |
| DE | 102012016820 A1 * | 4/2014 | ............ B60Q 5/005 |

(Continued)

OTHER PUBLICATIONS

Phelan, M., "Hyundai thinks new 2020 Sonata sound feature will keep drivers calm in traffic," Detroit Free Press Website, Available Online at https://www.freep.com/story/money/cars/mark-phelan/2019/12/10/2020-hyundai-sonata-nature-sounds/2627476001/, Dec. 10, 2019, 2 pages.

(Continued)

*Primary Examiner* — Chico A Foxx
(74) *Attorney, Agent, or Firm* — McCoy Russell LLP

(57) ABSTRACT

Systems and methods for generating sound elements in a vehicle are present. In one example, a method comprises selecting a sound element, the sound element corresponding to a natural environment; and broadcasting the sound element via one or more speakers of a vehicle. In this way, a sound environment may be provided to a vehicle user based on the at least one vehicle state.

19 Claims, 11 Drawing Sheets

(56) References Cited

U.S. PATENT DOCUMENTS

| | | | |
|---|---|---|---|
| 2010/0076968 A1* | 3/2010 | Boyns | G06F 16/29 |
| | | | 715/825 |
| 2012/0331093 A1* | 12/2012 | Cartier | G06Q 30/0269 |
| | | | 715/202 |
| 2013/0041648 A1* | 2/2013 | Osman | H04S 7/304 |
| | | | 381/300 |
| 2013/0158856 A1* | 6/2013 | Xiang | G01C 21/26 |
| | | | 701/408 |
| 2014/0086426 A1* | 3/2014 | Yamakawa | G10K 11/1754 |
| | | | 381/73.1 |
| 2015/0025662 A1* | 1/2015 | Di Censo | G06F 3/165 |
| | | | 700/94 |
| 2015/0120205 A1* | 4/2015 | Jeon | A61B 5/015 |
| | | | 702/19 |
| 2015/0160022 A1 | 6/2015 | Xiang | |
| 2018/0045530 A1* | 2/2018 | Hetherington | G01C 21/3629 |
| 2018/0132052 A1* | 5/2018 | Muench | H04R 3/005 |
| 2018/0181365 A1* | 6/2018 | Winton | H03G 3/32 |
| 2018/0242081 A1* | 8/2018 | Every | H04M 9/082 |
| 2019/0388647 A1* | 12/2019 | Bender | A61M 21/02 |
| 2020/0207358 A1* | 7/2020 | Katz | G06F 3/017 |
| 2021/0082388 A1* | 3/2021 | Hartmann | G10K 11/17857 |

FOREIGN PATENT DOCUMENTS

| | | | | |
|---|---|---|---|---|
| EP | 3416408 B1 | * | 12/2020 | F41H 7/02 |
| JP | 09319389 A | * | 12/1997 | |

OTHER PUBLICATIONS

European Patent Office, Partial European Search Report Issued in Application No. 20214046.3, dated May 27, 2021, Germany, 14 pages.

"Rainforest—Interactive Tropical Forest Soundscape," My Noise Website, Available Online at https://mynoise.net/NoiseMachines/rainforestNoiseGenerator.php, Available as Early as Jan. 29, 2016, 2 pages.

Trestain, C. et al., "Systems and Methods for External Environment Sensing and Rendering," U.S. Appl. No. 63/019,103, filed May 1, 2020, 53 pages.

Winton, R. et al., "Systems and Methods for Adjusting Activity Control Parameters," U.S. Appl. No. 16/950,670, filed Nov. 17, 2020, 59 pages.

Winton, R. et al., "Systems and Methods for Providing Nature Sounds," U.S. Appl. No. 17/112,684, filed Dec. 4, 2020, 84 pages.

* cited by examiner

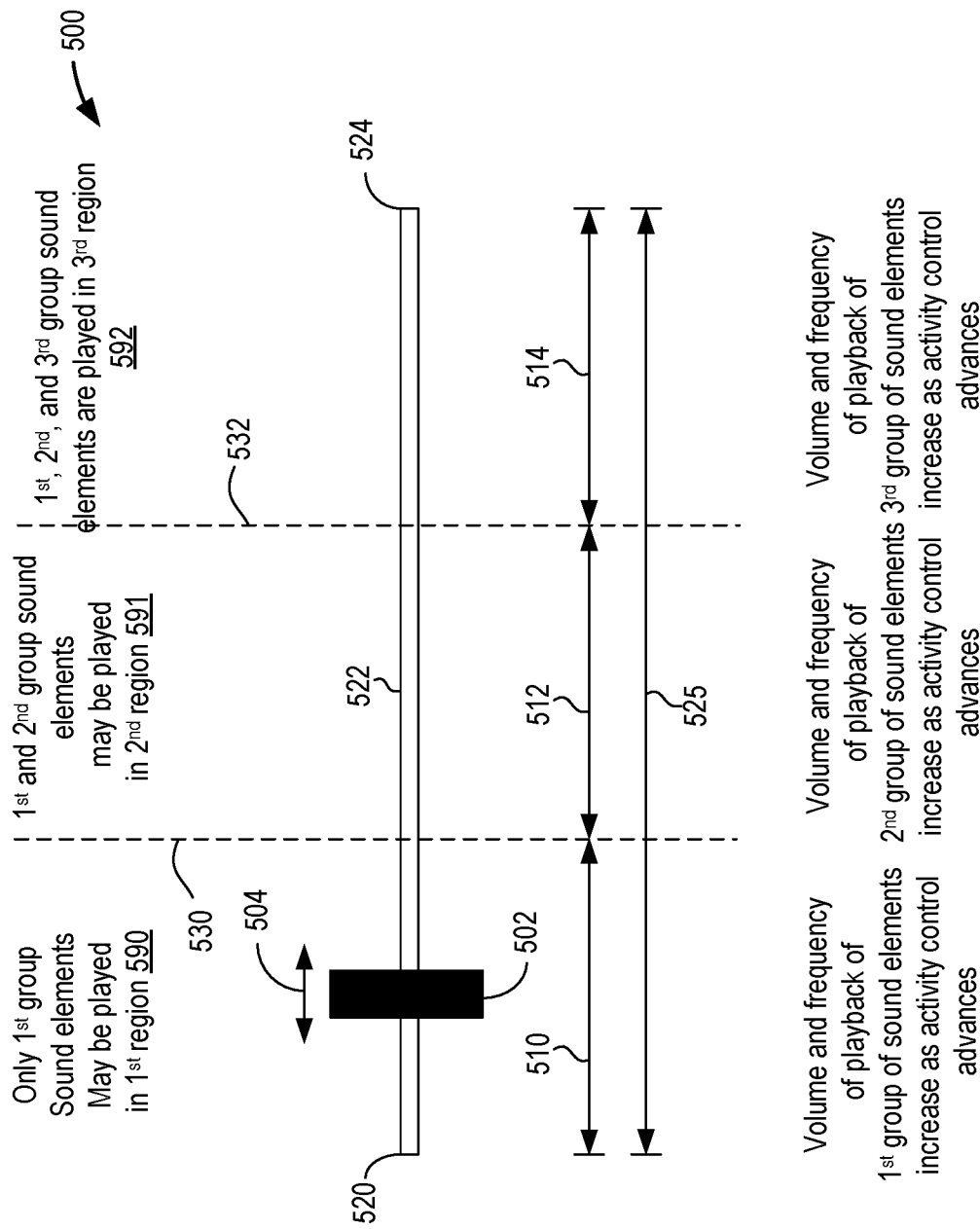

SYSTEMS AND METHODS FOR PROVIDING NATURE SOUNDS

CROSS REFERENCE TO RELATED APPLICATIONS

The present application claims priority to U.S. Provisional Application No. 62/954,195, entitled "SYSTEMS AND METHODS FOR ADJUSTING ACTIVITY CONTROL PARAMETERS", and filed on Dec. 27, 2019. The present application also claims priority to U.S. Provisional Application No. 63/026,621, entitled "SYSTEMS AND METHODS FOR PROVIDING NATURE SOUNDS", and filed on May 18, 2020. The entire contents of the above-listed applications are hereby incorporated by reference for all purposes.

BACKGROUND

The disclosure relates to sounds, which may be output in a vehicle.

SUMMARY

An in-vehicle entertainment system may be configured to play a plurality of recorded sounds (e.g., sound elements), including pre-recorded sound elements from natural settings and/or artificially generated sound elements imitating natural settings or evocative scenes. As an example, the in-vehicle entertainment system may include sound elements that, when played, reproduce sounds of rain falling, waterfalls, oceans, wildlife sound elements, wind, and the like. A user may input a request to play back such sound elements in order to increase a sensation of relaxation. For example, listening to sounds of natural settings may reduce stress and anxiety for vehicle users. As another example, a vehicle may be located in a scenic environment, and a user may desire a more immersive sonic experience.

The inventors have recognized the previously mentioned issues and have developed systems and methods to at least partially address the above issues. In particular, the inventors have developed a method for selecting a sound element, the sound element corresponding to a natural environment; and broadcasting the sound element via one or more speakers of a vehicle.

For example, by broadcasting sound elements based on the at least one vehicle state, natural sounds may be automatically played in the vehicle. For example, when a vehicle is travelling in a scenic area, sound elements corresponding to natural sounds in the scenic area may be broadcast, in order to incorporate elements of the exterior environment into the sound environment of the vehicle. Further, when an environmental condition, such as weather, is detected, sound elements corresponding to the environmental condition may be played in order to alert a user to changes in the environmental condition. As another example, a user may be stressed, such as due to a stressful driving environment (e.g., traffic), and sound elements corresponding to a more peaceful exterior environment may be played, thus reducing a stress level of the user. Further, each sound element played in the vehicle may be spatially mixed in order to create an immersive, surround sound experience. For example, each sound element may be indexed to a virtual location outside the vehicle, and the virtual location outside the vehicle may be mapped to a virtual speaker space inside the vehicle.

In this way, a sound environment inside a vehicle may be adjusted based on at least one state of a vehicle, such as a vehicle location, an environmental condition, and an emotional state (e.g., mood) of a user. For example, by adjusting the sound environment based on the at least one state of the vehicle, a user engagement with an exterior environment may be increased, which may increase user satisfaction while driving the vehicle. Further, in some examples, adjusting the sound environment based on the at least one state of the vehicle may decrease user stress levels by reducing an effect of a stressful exterior environment, such as while driving in traffic. Overall, user stress levels may be reduced while user satisfaction is increased.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 5B shows a schematic depiction of an activity control with example control regions;

DETAILED DESCRIPTION

Figure 1:
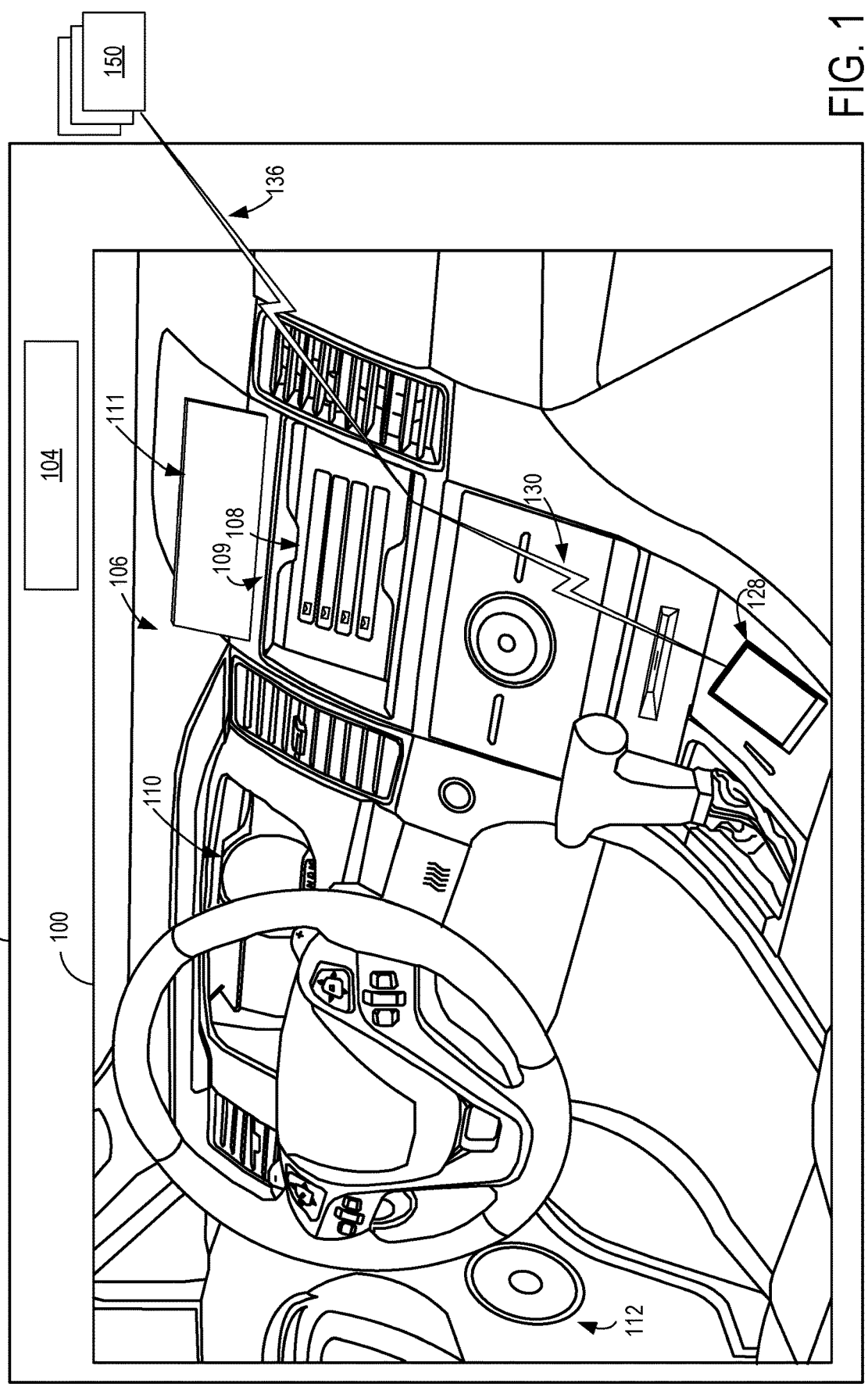
FIG. 1 shows an example partial view of a vehicle cabin in accordance with one or more embodiments of the present disclosure.
Figure 4:
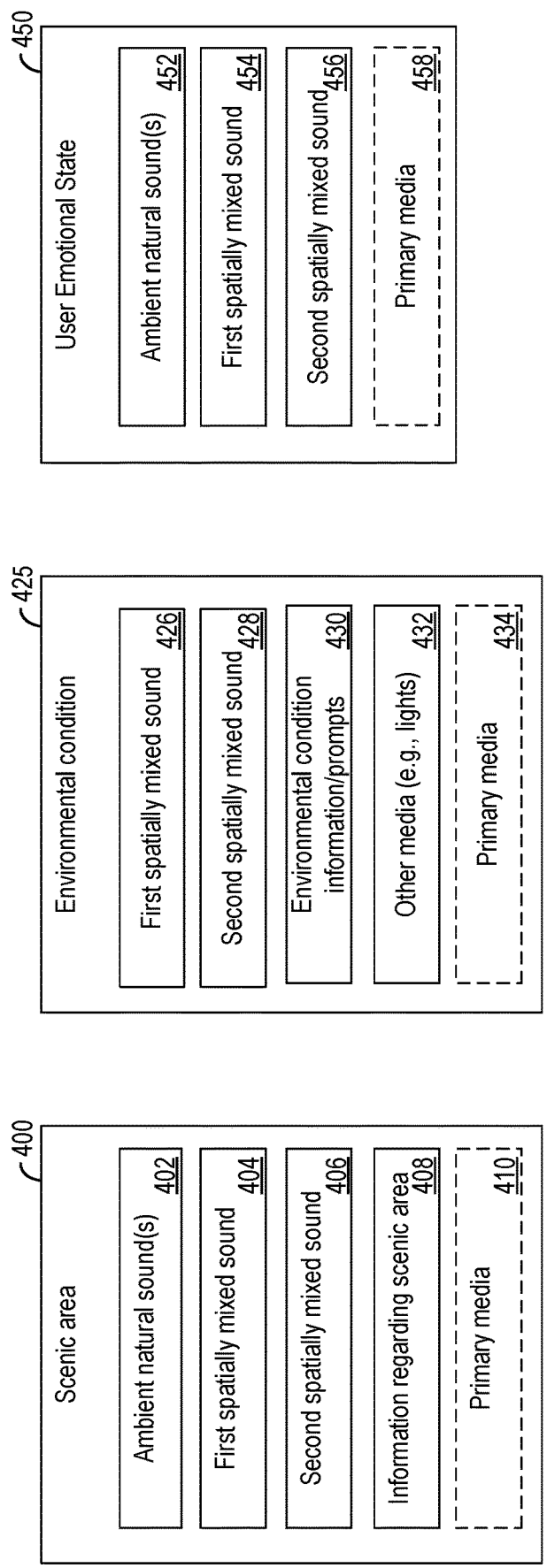
FIG. 4 shows example audio profiles for providing automated, spatially mixed sound in response to one of a scenic environment, an environmental condition, and a user emotional state.
Figure 5A:
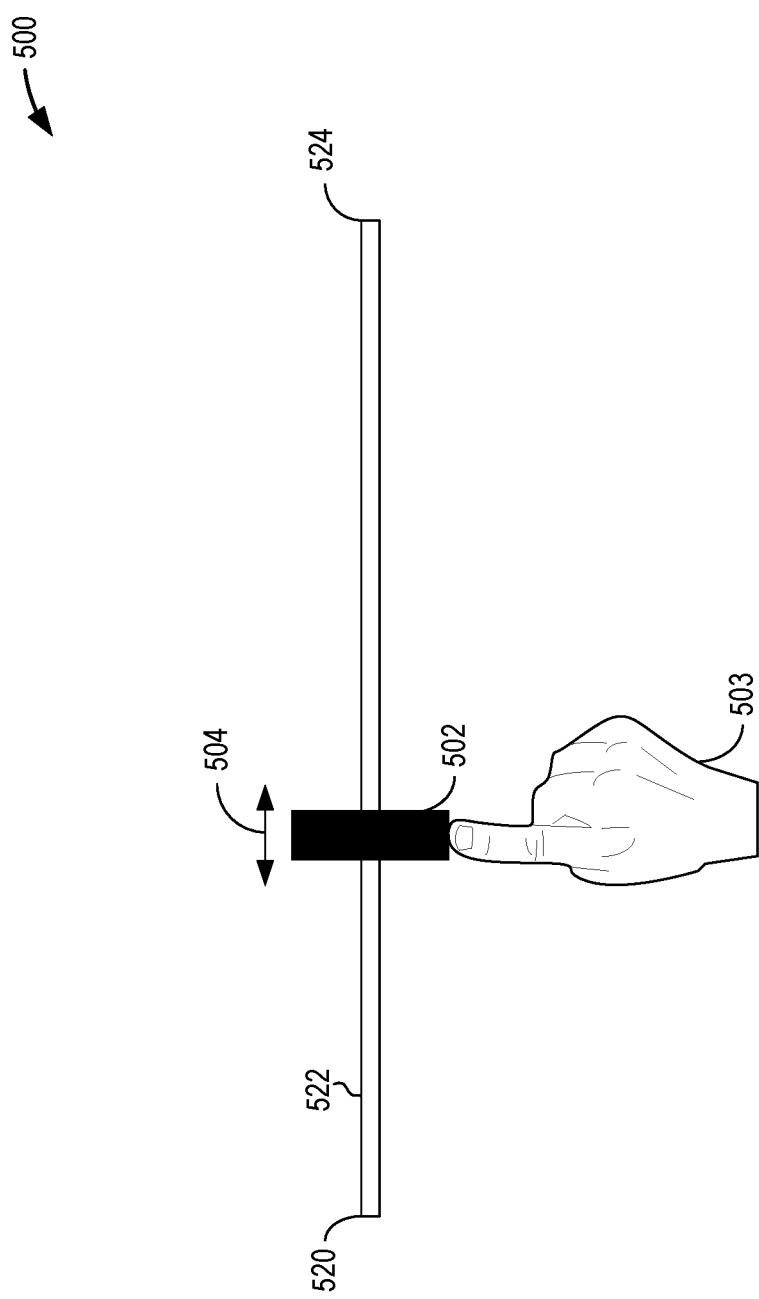
FIG. 5A shows a schematic depiction of an example activity control.

The present disclosure relates to providing an immersive sound environment in a vehicle, such as by automatically playing one or more pre-recorded sound elements (e.g., sound elements) based on operating conditions, and by spatially mixing the sound elements in order to increase sound immersion. For example, a vehicle system, such as shown in FIG. 1, may include an in-vehicle computing system, such as shown in more detail in FIG. 2. The in-vehicle computing system may be communicatively coupled to one or more remote servers, and may be configured to adjust audio settings of the vehicle based on vehicle operating conditions. Specifically, the vehicle system may include an audio system and a plurality of speakers, such as shown in FIG. 3, which may enable in-vehicle computing system to reproduce audio for users via a naturescape feature. Specifically, the in-vehicle computing system may monitor vehicle operating conditions, including a vehicle location, a traffic level, environmental conditions (e.g., such as weather), and upcoming stressors, and may automatically (e.g., in an automated fashion) select one or more pre-recorded audio files (e.g., environmental sound elements) based on the vehicle operating condition, and may play sound elements such as shown in FIG. 4, according to the method of FIGS. 7A and 7B. In some examples, environmental sound elements may be played via the audio system, such as in response to a user input, as shown in FIGS. 5A-6. Further, the in-vehicle computing system may adjust the audio system in order to provide spatial mixing, which may increase user immersion in the sound environment by reproducing a spatial arrangement of sound elements from a natural environment. FIG. 8 shows example scenes and corresponding sound elements that may be selected in response to the environmental triggers. In this way, an immersive, realistic soundscape may be provided for a vehicle user, which may increase user satisfaction while decreasing a stress level of the user.

Figure 2:
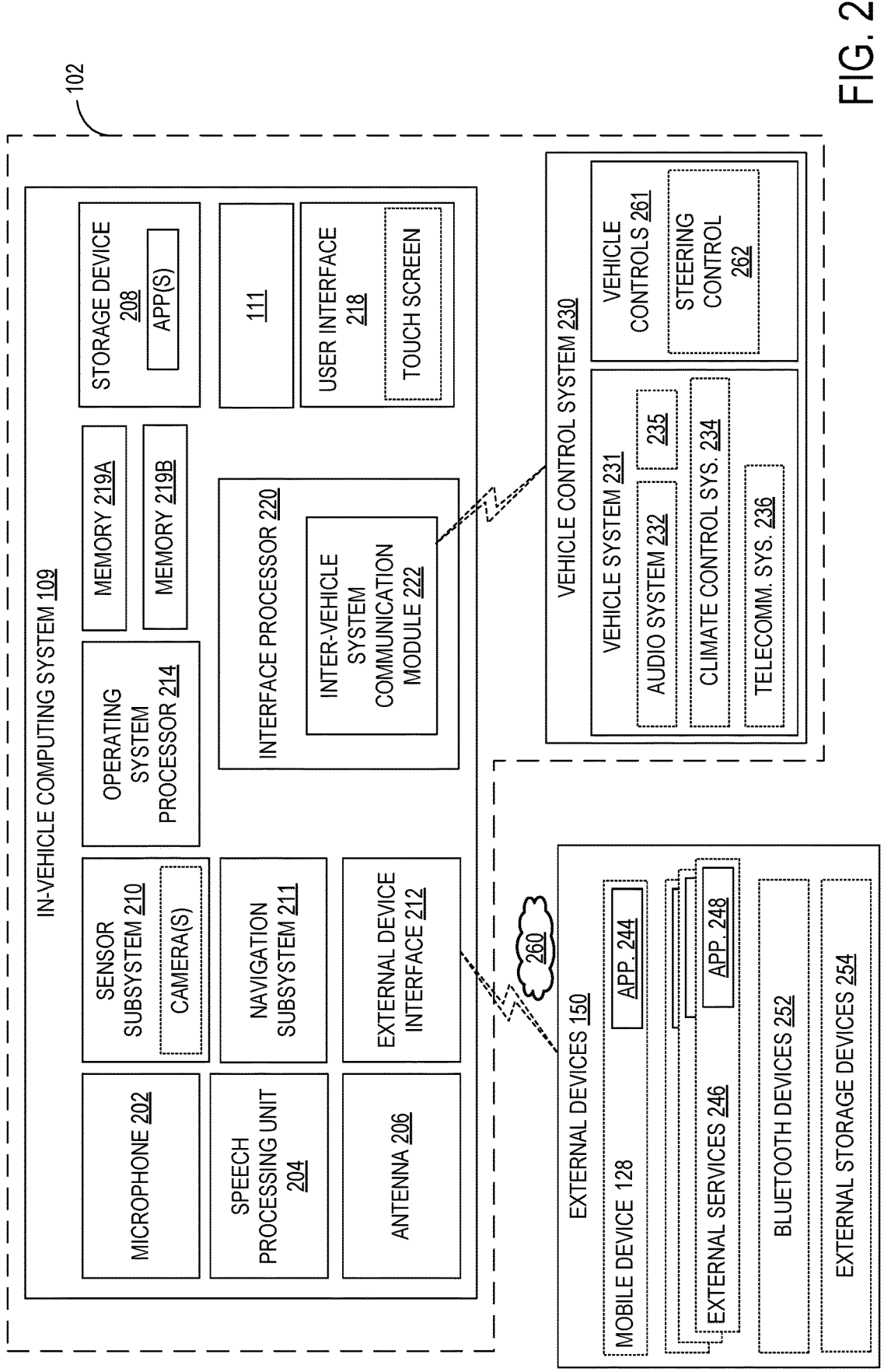
FIG. 2 shows an example in-vehicle computing system in accordance with one or more embodiments of the present disclosure.
Figure 3:
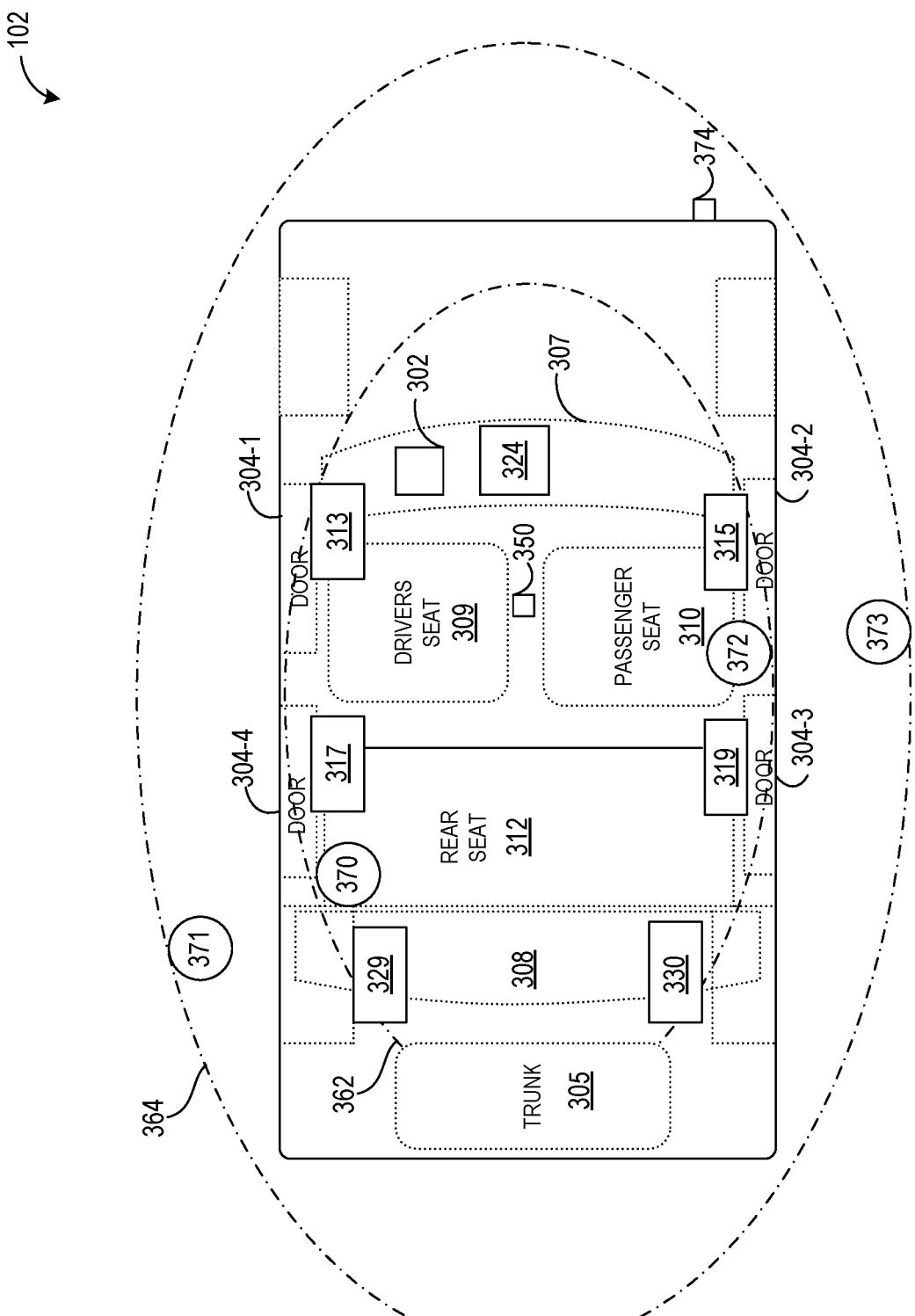
FIG. 3 shows an example sound processing system in a vehicle in accordance with one or more embodiments of the present disclosure.

As shown in FIGS. 1-3, a system according to the present disclosure may be part of a vehicle, and methods according to the present disclosure may be carried out via an in-vehicle computing system.

FIG. 1 shows an example partial view of one type of environment for an audio customization system: an interior of a cabin 100 of a vehicle 102, in which a driver and/or one or more passengers may be seated. Vehicle 102 of FIG. 1 may be a motor vehicle including drive wheels (not shown) and an internal combustion engine 104. Internal combustion engine 104 may include one or more combustion chambers which may receive intake air via an intake passage and exhaust combustion gases via an exhaust passage. Vehicle 102 may be a road automobile, among other types of vehicles. In some examples, vehicle 102 may include a hybrid propulsion system including an energy conversion device operable to absorb energy from vehicle motion and/or the engine and convert the absorbed energy to an energy form suitable for storage by an energy storage device. Vehicle 102 may include a fully electric vehicle, incorporating fuel cells, solar energy capturing elements, and/or other energy storage systems for powering the vehicle.

As shown, an instrument panel 106 may include various displays and controls accessible to a human driver (also referred to as the user) of vehicle 102. For example, instrument panel 106 may include a touch screen 108 of an in-vehicle computing system 109 (e.g., an infotainment system), an audio system control panel, and an instrument cluster 110. Touch screen 108 may receive user input to the in-vehicle computing system 109 for controlling audio output, visual display output, user preferences, control parameter selection, etc. While the example system shown in FIG. 1 includes audio system controls that may be performed via a user interface of in-vehicle computing system 109, such as touch screen 108 without a separate audio system control panel, in other embodiments, the vehicle may include an audio system control panel, which may include controls for a conventional vehicle audio system such as a radio, compact disc player, MP3 player, etc. The audio system controls may include features for controlling one or more aspects of audio output via speakers 112 of a vehicle speaker system.

For example, the in-vehicle computing system or the audio system controls may control a volume of audio output, a distribution of sound among the individual speakers of the vehicle speaker system, an equalization of audio signals, and/or any other aspect of the audio output. In further examples, in-vehicle computing system 109 may adjust a radio station selection, a playlist selection, a source of audio input (e.g., from radio or CD or MP3), etc., based on user input received directly via touch screen 108, or based on data regarding the user (such as a physical state and/or environment of the user) received via external devices 150 and/or mobile device 128. The audio system of the vehicle may include an amplifier (not shown) coupled to plurality of loudspeakers (not shown). In some embodiments, one or more hardware elements of in-vehicle computing system 109, such as touch screen 108, a display screen 111, various control dials, knobs and buttons, memory, processor(s), and any interface elements (e.g., connectors or ports) may form an integrated head unit that is installed in instrument panel 106 of the vehicle. The head unit may be fixedly or removably attached in instrument panel 106. In additional or alternative embodiments, one or more hardware elements of the in-vehicle computing system 109 may be modular and may be installed in multiple locations of the vehicle.

The cabin 100 may include one or more sensors for monitoring the vehicle, the user, and/or the environment. For example, the cabin 100 may include one or more seat-mounted pressure sensors configured to measure the pressure applied to the seat to determine the presence of a user, door sensors configured to monitor door activity, humidity sensors to measure the humidity content of the cabin, microphones to receive user input in the form of voice commands, to enable a user to conduct telephone calls, and/or to measure ambient noise in the cabin 100, etc. It is to be understood that the above-described sensors and/or one or more additional or alternative sensors may be positioned in any suitable location of the vehicle. For example, sensors may be positioned in an engine compartment, on an external surface of the vehicle, and/or in other suitable locations for providing information regarding the operation of the vehicle, ambient conditions of the vehicle, a user of the vehicle, etc. Information regarding ambient conditions of the vehicle, vehicle status, or vehicle driver may also be received from sensors external to/separate from the vehicle (that is, not part of the vehicle system), such as sensors coupled to external devices 150 and/or mobile device 128.

Cabin 100 may also include one or more user objects, such as mobile device 128, that are stored in the vehicle before, during, and/or after travelling. The mobile device 128 may include a smart phone, a tablet, a laptop computer, a portable media player, and/or any suitable mobile computing device. The mobile device 128 may be connected to the in-vehicle computing system via communication link 130. The communication link 130 may be wired (e.g., via Universal Serial Bus [USB], Mobile High-Definition Link [MHL], High-Definition Multimedia Interface [HDMI], Ethernet, etc.) or wireless (e.g., via BLUETOOTH, WIFI, WIFI direct, Near-Field Communication [NFC], cellular connectivity, etc.) and configured to provide two-way communication between the mobile device and the in-vehicle computing system. The mobile device 128 may include one or more wireless communication interfaces for connecting to one or more communication links (e.g., one or more of the example communication links described above). The wireless communication interface may include one or more physical devices, such as antenna(s) or port(s) coupled to data lines for carrying transmitted or received data, as well as one or more modules/drivers for operating the physical devices in accordance with other devices in the mobile device. For example, the communication link 130 may provide sensor and/or control signals from various vehicle systems (such as vehicle audio system, climate control system, etc.) and the touch screen 108 to the mobile device 128 and may provide control and/or display signals from the mobile device 128 to the in-vehicle systems and the touch screen 108. The communication link 130 may also provide power to the mobile device 128 from an in-vehicle power source in order to charge an internal battery of the mobile device.

In-vehicle computing system 109 may also be communicatively coupled to additional devices operated and/or accessed by the user but located external to vehicle 102, such as one or more external devices 150. In the depicted embodiment, external devices are located outside of vehicle 102 though it will be appreciated that in alternate embodiments, external devices may be located inside cabin 100. The external devices may include a server computing system, personal computing system, portable electronic device, electronic wrist band, electronic head band, portable music player, electronic activity tracking device, pedometer, smartwatch, GPS system, etc. External devices 150 may be connected to the in-vehicle computing system via communication link 136 which may be wired or wireless, as discussed with reference to communication link 130, and configured to provide two-way communication between the external devices and the in-vehicle computing system. For example, external devices 150 may include one or more sensors and communication link 136 may transmit sensor output from external devices 150 to in-vehicle computing system 109 and touch screen 108. External devices 150 may also store and/or receive information regarding contextual data, user behavior/preferences, operating rules, etc. and may transmit such information from the external devices 150 to in-vehicle computing system 109 and touch screen 108.

In-vehicle computing system 109 may analyze the input received from external devices 150, mobile device 128, and/or other input sources and select settings for various in-vehicle systems (such as climate control system or audio system), provide output via touch screen 108 and/or speakers 112, communicate with mobile device 128 and/or external devices 150, and/or perform other actions based on the assessment. In some embodiments, all or a portion of the assessment may be performed by the mobile device 128 and/or the external devices 150.

In some embodiments, one or more of the external devices 150 may be communicatively coupled to in-vehicle computing system 109 indirectly, via mobile device 128 and/or another of the external devices 150. For example, communication link 136 may communicatively couple external devices 150 to mobile device 128 such that output from external devices 150 is relayed to mobile device 128. Data received from external devices 150 may then be aggregated at mobile device 128 with data collected by mobile device 128, the aggregated data then transmitted to in-vehicle computing system 109 and touch screen 108 via communication link 130. Similar data aggregation may occur at a server system and then transmitted to in-vehicle computing system 109 and touch screen 108 via communication link 136/130.

FIG. 2 shows a block diagram of an in-vehicle computing system 109 configured and/or integrated inside vehicle 102. In-vehicle computing system 109 may perform one or more of the methods described herein in some embodiments. In some examples, the in-vehicle computing system 109 may be a vehicle infotainment system configured to provide information-based media content (audio and/or visual media content, including entertainment content, navigational services, etc.) to a vehicle user to enhance the operator's in-vehicle experience. The vehicle infotainment system may include, or be coupled to, various vehicle systems, subsystems, hardware components, as well as software applications and systems that are integrated in, or integratable into, vehicle 102 in order to enhance an in-vehicle experience for a driver and/or a passenger.

In-vehicle computing system 109 may include one or more processors including an operating system processor 214 and an interface processor 220. Operating system processor 214 may execute an operating system on the in-vehicle computing system, and control input/output, display, playback, and other operations of the in-vehicle computing system. Interface processor 220 may interface with a vehicle control system 230 via an inter-vehicle system communication module 222.

Inter-vehicle system communication module 222 may output data to other vehicle systems 231 and vehicle control elements 261, while also receiving data input from other vehicle components and systems 231, 261, e.g. by way of vehicle control system 230. When outputting data, inter-vehicle system communication module 222 may provide a signal via a bus corresponding to any status of the vehicle, the vehicle surroundings, or the output of any other information source connected to the vehicle. Vehicle data outputs may include, for example, analog signals (such as current velocity), digital signals provided by individual information sources (such as clocks, thermometers, location sensors such as Global Positioning System [GPS] sensors, etc.), digital signals propagated through vehicle data networks (such as an engine CAN bus through which engine related information may be communicated, a climate control CAN bus through which climate control related information may be communicated, and a multimedia data network through which multimedia data is communicated between multimedia components in the vehicle). For example, the in-vehicle computing system 109 may retrieve from the engine CAN bus the current speed of the vehicle estimated by the wheel sensors, a power state of the vehicle via a battery and/or power distribution system of the vehicle, an ignition state of the vehicle, etc. In addition, other interfacing means such as Ethernet may be used as well without departing from the scope of this disclosure.

A non-volatile storage device 208 may be included in in-vehicle computing system 109 to store data such as instructions executable by processors 214 and 220 in non-volatile form. The storage device 208 may store application data, including prerecorded sound elements, to enable the in-vehicle computing system 109 to run an application for connecting to a cloud-based server and/or collecting information for transmission to the cloud-based server. The application may retrieve information gathered by vehicle systems/sensors, input devices (e.g., user interface 218), data stored in volatile 219A or non-volatile storage device (e.g., memory) 219B, devices in communication with the in-vehicle computing system (e.g., a mobile device connected via a Bluetooth link), etc. In-vehicle computing system 109 may further include a volatile memory 219A. Volatile memory 219A may be random access memory (RAM). Non-transitory storage devices, such as non-volatile storage device 208 and/or non-volatile memory 219B, may store instructions and/or code that, when executed by a processor (e.g., operating system processor 214 and/or interface processor 220), controls the in-vehicle computing system 109 to perform one or more of the actions described in the disclosure.

A microphone 202 may be included in the in-vehicle computing system 109 to receive voice commands from a user, to measure ambient noise in the vehicle, to determine whether audio from speakers of the vehicle is tuned in accordance with an acoustic environment of the vehicle, etc. A speech processing unit 204 may process voice commands, such as the voice commands received from the microphone 202. In some embodiments, in-vehicle computing system 109 may also be able to receive voice commands and sample ambient vehicle noise using a microphone included in an audio system 232 of the vehicle.

One or more additional sensors may be included in a sensor subsystem 210 of the in-vehicle computing system 109. For example, the sensor subsystem 210 may include a camera, such as a rear view camera for assisting a user in parking the vehicle and/or a cabin camera for identifying a user (e.g., using facial recognition and/or user gestures). Sensor subsystem 210 of in-vehicle computing system 109 may communicate with and receive inputs from various vehicle sensors and may further receive user inputs. For example, the inputs received by sensor subsystem 210 may include transmission gear position, transmission clutch position, gas pedal input, brake input, transmission selector position, vehicle speed, engine speed, mass airflow through the engine, ambient temperature, intake air temperature, etc., as well as inputs from climate control system sensors (such as heat transfer fluid temperature, antifreeze temperature, fan speed, passenger compartment temperature, desired passenger compartment temperature, ambient humidity, etc.), an audio sensor detecting voice commands issued by a user, a fob sensor receiving commands from and optionally tracking the geographic location/proximity of a fob of the vehicle, etc. While certain vehicle system sensors may communicate with sensor subsystem 210 alone, other sensors may communicate with both sensor subsystem 210 and vehicle control system 230, or may communicate with sensor subsystem 210 indirectly via vehicle control system 230. A navigation subsystem 211 of in-vehicle computing system 109 may generate and/or receive navigation information such as location information (e.g., via a GPS sensor and/or other sensors from sensor subsystem 210), route guidance, traffic information, point-of-interest (POI) identification, and/or provide other navigational services for the driver.

External device interface 212 of in-vehicle computing system 109 may be coupleable to and/or communicate with one or more external devices 150 located external to vehicle 102. While the external devices are illustrated as being located external to vehicle 102, it is to be understood that they may be temporarily housed in vehicle 102, such as when the user is operating the external devices while operating vehicle 102. In other words, the external devices 150 are not integral to vehicle 102. The external devices 150 may include a mobile device 128 (e.g., connected via a Bluetooth, NFC, WIFI direct, or other wireless connection) or an alternate Bluetooth-enabled device 252. Mobile device 128 may be a mobile phone, smart phone, wearable devices/sensors that may communicate with the in-vehicle computing system via wired and/or wireless communication, or other portable electronic device(s). Other external devices include external services 246. For example, the external devices may include extra-vehicular devices that are separate from and located externally to the vehicle. Still other external devices include external storage devices 254, such as solid-state drives, pen drives, USB drives, etc. External devices 150 may communicate with in-vehicle computing system 109 either wirelessly or via connectors without departing from the scope of this disclosure. For example, external devices 150 may communicate with in-vehicle computing system 109 through the external device interface 212 over network 260, a universal serial bus (USB) connection, a direct wired connection, a direct wireless connection, and/or other communication link.

The external device interface 212 may provide a communication interface to enable the in-vehicle computing system to communicate with mobile devices associated with contacts of the driver. For example, the external device interface 212 may enable phone calls to be established and/or text messages (e.g., SMS, MMS, etc.) to be sent (e.g., via a cellular communications network) to a mobile device associated with a contact of the driver. The external device interface 212 may additionally or alternatively provide a wireless communication interface to enable the in-vehicle computing system to synchronize data with one or more devices in the vehicle (e.g., the driver's mobile device) via WIFI direct, as described in more detail below.

One or more applications 244 may be operable on mobile device 128. As an example, mobile device application 244 may be operated to aggregate user data regarding interactions of the user with the mobile device. For example, mobile device application 244 may aggregate data regarding music playlists listened to by the user on the mobile device, telephone call logs (including a frequency and duration of telephone calls accepted by the user), positional information including locations frequented by the user and an amount of time spent at each location, etc. The collected data may be transferred by application 244 to external device interface 212 over network 260. In addition, specific user data requests may be received at mobile device 128 from in-vehicle computing system 109 via the external device interface 212. The specific data requests may include requests for determining where the user is geographically located, an ambient noise level and/or music genre at the user's location, an ambient weather condition (temperature, humidity, etc.) at the user's location, etc. Mobile device application 244 may send control instructions to components (e.g., microphone, amplifier etc.) or other applications (e.g., navigational applications) of mobile device 128 to enable the requested data to be collected on the mobile device or requested adjustment made to the components. Mobile device application 244 may then relay the collected information back to in-vehicle computing system 109.

Likewise, one or more applications 248 may be operable on external services 246. As an example, external services applications 248 may be operated to aggregate and/or analyze data from multiple data sources. For example, external services applications 248 may aggregate data from one or more social media accounts of the user, data from the in-vehicle computing system (e.g., sensor data, log files, user input, etc.), data from an internet query (e.g., weather data, POI data), etc. The collected data may be transmitted to another device and/or analyzed by the application to determine a context of the driver, vehicle, and environment and perform an action based on the context (e.g., requesting/sending data to other devices).

Vehicle control system 230 may include controls for controlling aspects of various vehicle systems 231 involved in different in-vehicle functions. These may include, for example, controlling aspects of vehicle audio system 232 for providing audio entertainment to the vehicle occupants, aspects of climate control system 234 for meeting the cabin cooling or heating needs of the vehicle occupants, as well as aspects of telecommunication system 236 for enabling vehicle occupants to establish telecommunication linkage with others. For example, vehicle audio system 232 may provide a primary audio, such as music, talk radio, a podcast, audio from a movie, and the like. Further, vehicle audio system 232 may provide a secondary audio, such as natural sounds via a naturescape feature, as will be elaborated below with respect to FIG. 3.

Audio system 232 may include one or more acoustic reproduction devices including electromagnetic transducers such as speakers 235. Vehicle audio system 232 may be passive or active such as by including a power amplifier. In some examples, in-vehicle computing system 109 may be the only audio source for the acoustic reproduction device or there may be other audio sources that are connected to the audio reproduction system (e.g., external devices such as a mobile phone). The connection of any such external devices to the audio reproduction device may be analog, digital, or any combination of analog and digital technologies.

Climate control system 234 may be configured to provide a comfortable environment within the cabin or passenger compartment of vehicle 102. Climate control system 234 includes components enabling controlled ventilation such as air vents, a heater, an air conditioner, an integrated heater and air-conditioner system, etc. Other components linked to the heating and air-conditioning setup may include a windshield defrosting and defogging system capable of clearing the windshield and a ventilation-air filter for cleaning outside air that enters the passenger compartment through a fresh-air inlet.

Vehicle control system 230 may also include controls for adjusting the settings of various vehicle controls 261 (or vehicle system control elements) related to the engine and/or auxiliary elements within a cabin of the vehicle, such as steering wheel controls 262 (e.g., steering wheel-mounted audio system controls, cruise controls, windshield wiper controls, headlight controls, turn signal controls, etc.), instrument panel controls, microphone(s), accelerator/brake/clutch pedals, a gear shift, door/window controls positioned in a driver or passenger door, seat controls, cabin light controls, audio system controls, cabin temperature controls, etc. Vehicle controls 261 may also include internal engine and vehicle operation controls (e.g., engine controller module, actuators, valves, etc.) that are configured to receive instructions via the CAN bus of the vehicle to change operation of one or more of the engine, exhaust system, transmission, and/or other vehicle system. The control signals may also control audio output at one or more speakers 235 of the vehicle's audio system 232. For example, the control signals may adjust audio output characteristics such as volume, equalization, audio image (e.g., the configuration of the audio signals to produce audio output that appears to a user to originate from one or more defined locations), audio distribution among a plurality of speakers, etc. Likewise, the control signals may control vents, air conditioner, and/or heater of climate control system 234. For example, the control signals may increase delivery of cooled air to a specific section of the cabin.

Control elements positioned on an outside of a vehicle (e.g., controls for a security system) may also be connected to computing system 109, such as via communication module 222. The control elements of the vehicle control system may be physically and permanently positioned on and/or in the vehicle for receiving user input. In addition to receiving control instructions from in-vehicle computing system 109, vehicle control system 230 may also receive input from one or more external devices 150 operated by the user, such as from mobile device 128. This allows aspects of vehicle systems 231 and vehicle controls 261 to be controlled based on user input received from the external devices 150.

In-vehicle computing system 109 may further include an antenna 206. Antenna 206 is shown as a single antenna, but may comprise one or more antennas in some embodiments. The in-vehicle computing system may obtain broadband wireless internet access via antenna 206, and may further receive broadcast signals such as radio, television, weather, traffic, and the like. The in-vehicle computing system may receive positioning signals such as GPS signals via one or more antennas 206. The in-vehicle computing system may also receive wireless commands via FR such as via antenna (s) 206 or via infrared or other means through appropriate receiving devices. In some embodiments, antenna 206 may be included as part of audio system 232 or telecommunication system 236. Additionally, antenna 206 may provide AM/FM radio signals to external devices 150 (such as to mobile device 128) via external device interface 212.

One or more elements of the in-vehicle computing system 109 may be controlled by a user via user interface 218. User interface 218 may include a graphical user interface presented on a touch screen, such as touch screen 108 of FIG. 1, and/or user-actuated buttons, switches, knobs, dials, sliders, etc. For example, user-actuated elements may include steering wheel controls, door and/or window controls, instrument panel controls, audio system settings, climate control system settings, and the like. A user may also interact with one or more applications of the in-vehicle computing system 109 and mobile device 128 via user interface 218. In addition to receiving a user's vehicle setting preferences on user interface 218, vehicle settings selected by in-vehicle control system may be displayed to a user on user interface 218. Notifications and other messages (e.g., received messages), as well as navigational assistance, may be displayed to the user on a display of the user interface. User preferences/information and/or responses to presented messages may be performed via user input to the user interface.

FIG. 3 is a block diagram of a vehicle 102 that includes an example audio or sound processing system (AS) 302, which may include any or a combination of the sound processing systems and methods described below. The vehicle 102 includes doors 304, a driver seat 309, a passenger seat 310, and a rear seat 312. While a four-door vehicle is shown including doors 304-1, 304-2, 304-3, and 304-4, the audio system (AS) 102 may be used in vehicles having more or fewer doors. The vehicle 102 may be an automobile, truck, boat, or the like. Although only one rear seat is shown, larger vehicles may have multiple rows of rear seats. Smaller vehicles may have only one or more seats. While a particular example configuration is shown, other configurations may be used including those with fewer or additional components.

The audio system 302 (which may include an amplifier and/or other audio processing device for receiving, processing, and/or outputting audio to one or more speakers of the vehicle) may improve the spatial characteristics of surround sound systems. The audio system 302 supports the use of a variety of audio components such as radios, COs, DVDs, their derivatives, and the like. The audio system 302 may use 2-channel source material such as direct left and right, 5.1 channel, 6.2 channel, 7 channel, 12 channel and/or any other source materials from a matrix decoder digitally encoded/decoded discrete source material, and the like. The audio system 302 may utilize multiple audio channels. For example, audio system 302 may utilize a first channel for primary media, such as one or more of warning, media, navigational, and telephone/telematics sound elements. Further, a second channel may be used for secondary media (e.g., provided by a naturescape feature). As such, both primary media and secondary media may be played substantially simultaneously via audio system 302.

The amplitude and phase characteristics of the source material and the reproduction of specific sound field characteristics in the listening environment both play a key role in the successful reproduction of a surround sound field. As such, the audio system 302 may increase the reproduction of a surround sound field by controlling the sound delay time, surround upmixer parameters (e.g., wrap, reverb room size, etc.), amplitude, phase, and mixing ratio between discrete and passive decoder surround signals and/or the direct two-channel output signals, in at least one example. The amplitude, phase, and mixing ratios may be controlled between the discrete and passive decoder output signals. The spatial sound field reproduction may be increased for all seating locations by re-orientation of the direct, passive, and active mixing and steering parameters, especially in a vehicle environment.

The mixing and steering ratios as well as spectral characteristics may be adaptively modified as a function of the noise and other environmental factors. For example, the mixing and steering ratios may be adjusted based on a sensed sound level external to the vehicle. As another example, the mixing and steering ratios may be adjusted based on an estimated engine noise generated by the vehicle, such as by increasing a volume in response to increased engine noise. In a vehicle, information from the data bus, microphones, and other transduction devices may be used to control the mixing and steering parameters.

The vehicle 102 has a front center speaker (CTR speaker) 324, a front left speaker (FL speaker) 313, a front right speaker (FR speaker) 315, and at least one pair of surround speakers.

The surround speakers may be a left side speaker (LS speaker) 317 and a right side speaker (RS speaker) 319, a left rear speaker (LR speaker) 329 and a right rear speaker (RR speaker) 330, or a combination of speaker sets. Other speaker sets may be used. While not shown, one or more dedicated subwoofers or other drivers may be present. Possible subwoofer mounting locations include the trunk 305, below a seat, or the rear shelf 308. The vehicle 102 may also have one or more microphones 350 mounted in the interior. For example, at least one microphone may be mounted near each seat of the vehicle in order to capture audio from users, such as voice commands.

Each CTR speaker, FL speaker, FR speaker, LS speaker, RS speaker, LR speaker, and RR speaker may include one or more transducers of a predetermined range of frequency response such as a tweeter, a mid-range, or a woofer. The tweeter, mid-range, or woofer may be mounted adjacent to each other in essentially the same location or in different locations. For example, the FL speaker 313 may be a tweeter located in door 304-1 or elsewhere at a height roughly equivalent to a side mirror or higher. The FR speaker 315 may have a similar arrangement to FL speaker 313 on the right side of the vehicle (e.g., in door 304-2).

The LR speaker 329 and the RR speaker 330 may each be a woofer mounted in the rear shelf 308. The CTR speaker 324 may be mounted in the front dashboard 307, in the roof, on or near the rear-view mirror, or elsewhere in the vehicle 102. In other examples, other configurations of loudspeakers with other frequency response ranges are possible. In some embodiments, additional speakers may be added to an upper pillar in the vehicle to enhance the height of the sound image. For example, an upper pillar may include a vertical or near-vertical support of a car's window area. In some examples, the additional speakers may be added to an upper region of an "A" pillar toward a front of the vehicle.

Further still, in some examples, one or more speakers may be incorporated into a seat of the vehicle (e.g., one of driver seat 309, passenger seat 310, and rear seat 312) in order to increase a sonic quality. For example, a speaker may be integrated into a headrest of each of the driver seat 309, the passenger seat 310, and the rear seat 312. For example, left speaker 329 may be incorporated into a headrest of rear seat 312, and right speaker 330 may be incorporated into the headrest of rear seat 312. As another example, FL speaker 313 may be incorporated into a headrest of driver seat 3-9, and FR speaker 315 may be incorporated into a headrest of passenger seat 310. For example, incorporating speakers into headrests of the vehicle seats may enable more targeted sound mixing, such as increasing a media volume for a first user without significantly affecting the media volume for a second user. Further, incorporating speakers into headrests of vehicle seats may increase a user immersion in the media, such as in the environmental sound elements reproduced via audio system 302.

To enhance a media experience for occupants of the vehicle 102, the audio system 302 may include a naturescape feature. When the naturescape feature is activated, the audio system 302 may reproduce a plurality of sound elements (e.g., as secondary media via the second channel), such as pre-recorded natural sound elements and artificially generated reproductions of natural sound elements. The plurality of sound elements may be calibrated to provide a sonic representation of a natural environment or natural scene, such as a remote natural environment or an environment outside the vehicle. In some examples the plurality of sound elements may be provided in response to a user input (e.g., in a manual mode of the naturescape feature), while in other examples, the plurality of sound elements may be provided based on sensor data (e.g., in an automated mode of the naturescape feature). In the manual mode of the naturescape feature, a user may select a natural scene with associated sound elements, and the user may adjust a volume and frequency of the associated sound elements. Embodiments of the manual mode of the naturescape feature will be elaborated with respect to FIGS. 5A-6. In the automated mode of the naturescape feature, the in-vehicle computing system may determine one or more states associated with the vehicle 102 based on the sensor data (e.g., such as a vehicle location, an environmental condition, and an emotional state of a user), and may determine sound elements to play based on the one or more states.

Both primary media (e.g., such as music, a voice call, talk radio, and the like) and secondary media (e.g., provided by the naturescape feature) may be played via audio system 302. In some examples, the secondary media may be layered over the primary media without any adjustment to each of the primary media and the secondary media. As another example, the primary media may be ducked in response to the secondary media playing, in order to reduce a total audio volume in the vehicle, and to enhance sound quality of the secondary media. In some examples, an amount of ducking may be adjusted based on a media type. For example, talk radio may be ducked less than music, due to the wider sonic spectrum of music relative to the sonic spectrum of talk radio. As another example, the secondary media may be muted during a voice call (e.g., over the primary media channel) in order to increase clarity of the voice call.

However, in some examples, a user may select to maintain the secondary media on during a voice call in order to share the sonic experience via the voice call.

Further, in each of the manual mode of the naturescape feature and the automated mode of the naturescape feature, spatial mixing may be used to provide an immersive, three-dimensional sound environment. For example, sound elements may be spatially mixed so that each sound element is perceived as originating in a spatial location. For example, wildlife sounds (e.g., such as bird sounds) may be spatially mixed so that the wildlife sounds are perceived to originate from a distinct spatial location. For example, each sound element may be continuously mapped to a virtual speaker region 362 or a distinct speaker element, and the virtual speaker region and/or each speaker may be adjusted in order to reproduce the perceived spatial location of the sound element. For example, each sound element may be indexed to a virtual location in a virtual sound space 364 (e.g., representing a space around the vehicle 102), and there may be a 1:1 mapping between the virtual sound space and the virtual speaker region 362. For example, the in-vehicle computing system may adjust audio gains, panning settings, and other audio settings for each speaker of audio system 302 based on the virtual location of the sound element. Further, the desired sound location may be perceived as inside or outside the vehicle cabin. As a first example, the virtual location in the virtual sound space 364 may be a location outside the vehicle. As a second example, the virtual location in the virtual sound space 364 may be inside the vehicle.

Further, in some examples, the composition of sound elements and/or the virtual spatial location of the sound element(s) may be adjusted based on vehicle characteristics such as movement, speed, location, or proximity. As an example, as a vehicle drives through a scenic environment, various sound elements may be adjusted to give the impression of movement. For example, as a vehicle moves closer to a waterfall, a sound element corresponding to a waterfall may increase in volume. As another example, as a vehicle moves laterally, a wildlife sound may be panned from a first side of the vehicle to a second side of the vehicle. By spatially mixing sound elements, a surround-sound, immersive experience may be provided to the user, which may increase user satisfaction.

Sound elements may be considered synthetic (e.g., not corresponding to a sound in the environment outside the vehicle) or real (e.g., corresponding to a sound in the environment outside the vehicle), and may be spatially mixed to be perceived as spatially located. As a non-limiting example, a first sound element may represent a birdcall, and may be played via audio system 302 in response to a vehicle location. For example, the birdcall may be a synthetic sound, and may not correspond to a specific birdcall detected outside the vehicle. The birdcall may be indexed to a virtual location 371 in a virtual sound space 364 surrounding the vehicle. The virtual location in the virtual sound space may be mapped to a location in the virtual speaker region 362, such as location 370. In order to spatially mix the first sound element, the first sound element may be panned to the left side speaker 317 and the left rear speaker 329. For example, the audio gain for the first sound element may be highest for the left side speaker 317 and the left rear speaker 329, and may be lower for other speakers of the vehicle. For example, each sound element may be perceived to originate from a spatial location due to a known relationship between audio panning and perceived spatial location, such as a surround sound technique known in the art (e.g., such as 5.1 surround sound, 7.1 surround sound, ambisonic surround sound, and the like). Further, some sound elements may be spatially mixed by upmixing one or two channels to multiple speakers.

As another non-limiting example, a second sound element may represent a real sound detected outside the vehicle. For example, a microphone 374 may be coupled to an exterior of the vehicle, and may be configured to detect real sounds. In response to detecting a desirable natural sound, such as thunder, the second sound element may be played inside the vehicle to represent the natural sound. In some examples, the sound element may be a recording of the external sound captured by microphone 374, and in other examples, the sound element may be a pre-recorded or computer generated representation of the external sound, such as a pre-recorded sound file of thunder. The thunder may be indexed to a virtual location 373 in the virtual sound space 364 surrounding the vehicle. The virtual location in the virtual sound space may be mapped to a location in the virtual speaker region 362, such as location 372. In order to spatially mix the second sound element, the second sound element may be panned primarily to the right side speaker 319 and the right front speaker 315. For example, the audio gain for the first sound element may be highest for the right side speaker 319 and the right front speaker 315, and may be lower for other speakers of the vehicle.

Some sound elements may be spatially mixed as ambient sounds. For example, a third sound element may represent rain sounds, and may be spatially mixed to be perceived as surrounding the vehicle. For example, the third sound element may be played at approximately the same volume via each speaker of vehicle 102, according to surround sound techniques known in the art.

In this way, each sound element may be perceived to originate from a spatial location due to a known relationship between audio panning and perceived spatial location, such as a surround sound technique known in the art (e.g., such as 5.1 surround sound, 7.1 surround sound, ambisonic surround sound, and the like). Some sound elements may be real sound elements, and may correspond to sounds detected outside the vehicle (e.g. such as by microphone 374). Other sound elements may be synthetic sound elements, and may not directly correspond to sounds detected outside the vehicle. Further, some sound elements may be spatially mixed by upmixing two channels to multiple speakers. For example, a sound element may have been recorded via a two-track recording device, but may be upmixed to the plurality of speakers in vehicle 102 in order to be perceived as a surround sound.

In some examples, audio system 302 may be in the automated mode of the naturescape feature, and may provide sound elements based on one or more states of the vehicle. Turning now to FIG. 4, three vehicle states are shown, with associated audio profiles for each vehicle state. For example, the vehicle may be vehicle 102 of FIGS. 1-3, and may be operated by at least one user. The one or more states associated with the vehicle may include, as non-limiting examples, a weather outside the vehicle, a speed of the vehicle, an environment in which the vehicle is traveling, an occupancy state of the vehicle, an emotional state (e.g., mood) of one or more occupants of the vehicle, and a geographic location of the vehicle. In particular, in-vehicle computing system may monitor for the presence of the vehicle in a scenic area 400 (e.g., such as a park, a beach, a historical location, a forest, and the like), for an environmental condition 425 (e.g., a weather-related change such as one of an approaching storm and a heat wave), and an emotional state 450 of one or more vehicle occupants (e.g., such as anxiety due to traffic).

If the vehicle is determined to be in a scenic area 400, a plurality of sound elements may be provided. Specifically, based on the detected scenic area, an in-vehicle computing system may select and/or generate sound elements in order to bring the exterior environment into the vehicle through an immersive sonic experience. For example, ambient natural sound(s) 402 may be played, such as ambient sounds associated with the detected scenic area, such as rain, wind, waves, and the like. Further, a plurality of spatially mixed sounds may be perceived to originate from a distinct location, such as the first spatially mixed sound 404 and the second spatially mixed sound 406. Further still, information regarding the scenic area 408 may be provided in order to enrich a user experience of the scenic area. For example, the in-vehicle computing system may access facts relating to the detected scenic area, and may provide the facts to the user. While providing this secondary media due to the scenic area, primary media 410 may optionally continue to play via the audio system. For example, the primary media 410 may be adjusted based on the secondary media.

If the environmental condition 425 is detected, a plurality of sound elements may be provided. For example, the environmental condition may be a weather-related change, and the naturescape feature may alert the user to the changing environmental conditions. For example, a plurality of spatially mixed sound elements, such as the first spatially mixed sound element 426 and the second spatially mixed sound element 428, may be provided in order to alert a user to a type of environmental change and a location of the environmental change. Further, information and/or warning regarding the environmental change 430 may be provided. In some examples, other media 432, such as lights, may be provided in order to further alert the user to the environmental change. For example, lights may reproduce the effect of lightening, or a warning light may flash to alert a user to a temperature change.

If the user emotional state 450 is detected (e.g., such as user stress or another undesirable user mood), natural sounds may be provided in order to reduce user stress and increase user enjoyment. For example, although a user may be driving through traffic, sounds of an ocean beach may be provided. For example, ambient natural sound(s) 452 (e.g., such as ocean waves) may create a baseline of a stress-relieving sound environment, and spatially mixed sounds, such as a first spatially mixed sound 454 and a second spatially mixed sound 456, may increase the verisimilitude of the sound environment by providing spatially located sound elements. Further, primary media 458 may continue to play in order to minimize disruption of the user experience. For example, the primary media 458 and the secondary media may be mixed so that the primary media 458 remains audible, while the secondary media decreases user stress by reducing the influence of a stressful external environment. Further, the controller may adjust the secondary media based on a combination of vehicle conditions. For example, the controller may provide secondary media based on a scenic area, but may further adjust the secondary media based on an emotional state of the user. As another example, the controller may provide secondary media based on an environmental condition, but may adjust the secondary media based on the emotional state of the user.

Thus, based on a state associated with the vehicle, as determined by the in-vehicle computing system based on vehicle conditions and/or user inputs, the in-vehicle computing system may adjust the audio system in order to provide an immersive sonic experience. Stated differently, the in-vehicle computing system may alter the sound environment in the vehicle cabin by playing sound elements corresponding to a natural environment or natural scene. Thus, in some examples, the in-vehicle computing system may increase augmentation of external environmental sounds, while in other examples the in-vehicle computing system may decrease, or even stop, augmentation of external environmental sounds. As an example, the sound elements may be calibrated to enhance a user's experience of a current vehicle location. For example, the vehicle may be driving through a scenic area, such as one of a park, a forest, a beach, and a wildlife preserve. In order to enhance the user's experience of this scenic area, sound elements corresponding to the scenic area may be provided, such as ambient nature sound elements (e.g., such as wind and rain), wildlife sound elements, and the like. Further, information regarding the scenic environment may be provided. As another example, in response to an environmental change, such as an approaching storm, sound elements corresponding to the environmental change (e.g., such as pre-recorded thunder) and a warning message may be provided in order to alert the user to the environmental change. In this way, features of an environment outside the vehicle may be brought in via the vehicle audio system, increasing user integration with the outside environment.

However, in some examples, the opposite effect may be desired, and a user may want to reduce the impact of the external environment. For example, the vehicle may be in traffic, or may be located in a stressful urban environment. Such environments may increase a stress level of a user, which may decrease user satisfaction. Therefore, sound elements corresponding to a remote location may be preferred. For example, while a user is in traffic in an urban environment, sound elements corresponding to a peaceful forest may be provided, such as one or more of a gentle breeze, a waterfall, and a bird song. In this way, user stress may be reduced. In some examples, user stress may be estimated based on navigation data, such as from a navigation subsystem (e.g., navigation subsystem 211 of FIG. 2). For example, when the in-vehicle computing system determines that the vehicle is in heavy traffic (e.g., based on the navigation data), the in-vehicle computing system may determine that a user emotional state includes stress. Further, in some examples, a user stress level may be determined based on biometric data, such as from an infrared camera, a camera configured to detect emotional state based on facial expression, a wearable device monitoring heart rate and body temperature, and the like, and sound elements may be played in response to the user stress level exceeding a threshold user stress level.

Next, FIGS. 5A-6 show embodiments for the manual mode of the naturescape feature, in which sound elements corresponding to a natural environment (e.g., secondary media) are provided in response to a user input. For example, while operating in the manual mode, an activity control may be provided to a user for controlling the sound elements. For example, sound elements may be provided in response to a user input via the activity control. Turning now to FIG. 5A, one example of an activity control 500 is shown. The activity control 500 may be displayed on a touch screen (e.g., 108 of FIG. 1) or mobile device 128. Alternatively, activity control 500 may be realized as a three dimensional device that is part of audio system 232 of FIG. 2. In this example, activity control 500 takes a form of a slider control that includes a slider bar 502 and a slide bar guide 522. However, in other examples, activity control 500 may be realized in the form of a rotary knob or other known user input device without departing from the scope or intent of the present description. A position or state of activity control 500 may refer to a position or state of slider bar 502.

Slider bar 502 may be moved longitudinally along the length of slide bar guide 522 as indicated by arrows 504 by human user 503. Slider bar 502 may be moved to a left extent 520 or a right extent 524 to adjust sound activity that may be associated with a particular scene that may be shown via display 111 of FIG. 1. For example, a user may wish to relax by listening to prerecorded sound elements of rain falling, waves crashing on a seashore, or water rushing down a creek. The user may select which sound to play back over vehicle speakers and a visual representation of the sound may be displayed on a display panel. Attributes of the sound that is selected for playback over vehicle speakers may be adjusted according to a position of slider bar 502, or of an operating state of the activity control, as described in further detail in the descriptions of FIGS. 5B-6.

Slider bar 502 may be in a base position when it is moved left to extent 520. Slider bar 502 may be fully advanced when it is moved right to extent 524. In one example, lowest level outputs of controlled sound elements or features may be output when slider bar 502 is positioned at the left extent 520. Greatest or highest level outputs of controlled sound elements or features may be output when slider bar 502 is positioned at the right extent 524.

Referring now to FIG. 5B, an activity control 500 that includes a plurality of control regions is shown. In this example, activity control 500 includes three control regions; however, in other examples, the actual total number of control regions may be greater than three or less than three. Further, in this example, the control regions each comprise about one third of the length of slide bar guide 522, but the control regions may be adjusted according to other dimensions, if desired. The control range or range of authority of activity control 500 is indicated by arrow 525 and it spans the three control regions.

A first control region 590 for slide bar 502 begins at a left extent 520 of slide bar guide 522 and ends at vertical line 530. Leader 510 shows the range of first control region 590. Slide bar 502 is shown in the first control region 590, so the computing system 109 shown in FIG. 1 or audio system 232 shown in FIG. 2 may play back sound elements digitally stored in non-volatile memory that are included in a first group of sound elements that are associated with a particular theme, scene, or environment that has been selected by a user. A theme may be a mood or state of mind that is being conveyed (e.g., relax, high emotional energy, be happy, etc.). The sound elements may be played back or broadcast through the vehicle speakers. The first group of sound elements may be characterized as steady-state sound elements. Steady-state sound elements may include but are not limited to the sound of falling rain drops, the sound of waves crashing on a seashore, the sound of crickets softly chirping, the sound of a soft breeze, and other sound elements intended to capture the essence of a mode or the selected theme, scene, or environment. Steady-state sound elements may be perceived by users as being continuous.

The position of slide bar 502 within the first control region 590 may define the volume or sound power output level of the speakers and the frequency of playback or density for the steady-state sound elements that are included in the selected scene or environment. For example, if the slide bar is positioned at the left extent of slide bar guide 522, then steady-state sound elements in the selected theme, scene, or environment may be played back at a low frequency of repetition (e.g., a rain falling sound sequence retrieved from memory may repeat at a rate of 0.03 Hz) and a very low volume or sound power output level. If the slide bar 502 is moved to the right and stopped before the slide bar enters the second control region 591, then the same steady-state sound elements may be played back at a higher frequency (e.g., 0.1 Hz) and a low volume or sound power level. Thus, as slide bar 502 is moved from left to right while in the first control region, the amount of sound power and frequency of playback of steady-state sound elements is increased.

A second control region 591 for slide bar 502 begins at the vertical line 530 and it ends at vertical line 532. Leader 512 shows the range of second control region 591. In one example, when slide bar 502 enters the second control region 591, the volume or sound power output of steady-state sound elements is maintained at its most recent level and the stead-state sound elements frequency of playback is maintained at its most recent level. The computing system 109 shown in FIG. 1 or audio system 232 shown in FIG. 2 may begin to play back sound elements stored in non-volatile memory that are included in a second group of sound elements that are associated with the selected particular theme, scene, or environment. The sound elements may be played back or broadcast through the vehicle's speakers. The second group of sound elements may be characterized as dynamic sound elements. Dynamic sound elements may include but are not limited to the sound birds calling, the sound of distant thunder, the sound of owls hooting, and similar sound elements emulating the wildlife and fauna included in the selected theme, scene, or environment. Dynamic sound elements may have a perceived characteristic of not being continuous.

The position of slide bar 502 within the second control region 591 may define the volume or sound power output level of the speakers and the frequency of playback or density for the dynamic sound elements that are included in the selected theme, scene, or environment. For example, if the slide bar 502 is positioned just to the right of line 530, then steady-state sound elements in the selected theme, scene, or environment may be played back at their frequency of repetition and volume or sound power output when slide bar 502 reached the positon of line 530. The dynamic sound elements in the selected theme, scene, or environment may be played back at a low frequency of repletion and a low volume or sound power output when slide bar 502 is positioned just to the right of line 530.

If the slide bar 502 is moved to the right and stopped just before the slide bar reaches a position of vertical line 532, then steady-state sound elements in the selected theme, scene, or environment may continue to be played back at their frequency of repetition and volume or sound power output when slide bar 502 reached the positon of line 530. The dynamic sound elements in the selected theme, scene, or environment may be played back at a higher frequency of repletion and a higher volume or sound power output than when slide bar 502 is positioned just to the left of line 530.

A third control region 592 for slide bar 502 begins at the vertical line 532 and it ends at the right extent 524 of slide bar guide 522. Leader 514 shows the range of third control region 592. In one example, when slide bar 502 enters the third control region 592, the volume or sound power output of steady-state sound elements and dynamic sound elements may be maintained at their most recent levels and the stead-state and dynamic sound elements frequency of playback may be maintained at their most recent levels. The computing system 109 shown in FIG. 1 or audio system 232 shown in FIG. 2 may begin to play back sound elements stored in non-volatile memory that are included in a third group of sound elements that are associated with the selected particular theme, scene, or environment. The sound elements may be played back or broadcast through the vehicle's speakers. The third group of sound elements may be characterized as surreal sound elements. Surreal sound elements may include but are not limited to the sound of coyotes howling, the sound of elk bugling, the sound of thunder claps, and other unnatural sound elements intended to augment the user's emotional response to the selected theme, scene, or environment.

The position of slide bar 502 within the third control region 592 may define the volume or sound power output level of the speakers and the frequency of playback or density for the surreal sound elements that are included in the selected theme, scene, or environment. For example, if the slide bar 502 is positioned just to the right of line 532, then steady-state and dynamic sound elements in the selected theme, scene, or environment may be played back at their frequency of repetition and volume or sound power output when slide bar 502 reached the positon of line 532. The surreal sound elements in the selected theme, scene, or environment may be played back at a low frequency of repletion and a low volume or sound power output when slide bar 502 is positioned just to the right of line 532.

If the slide bar 502 is moved to the right and stopped just before the slide bar reaches the extent 524 of slide bar guide 522, then steady-state and dynamic sound elements in the selected theme, scene, or environment may continue to be played back at their frequency of repetition and volume or sound power output when slide bar 502 reached the positon of line 532. The surreal sound elements in the selected theme, scene, or environment may be played back at a higher frequency of repletion and a higher volume or sound power output than when slide bar 502 is positioned just to the right of line 532.

Thus, a sole activity control may be the basis for increasing a complexity of sound elements generated via computing system 109 shown in FIG. 1 or audio system 232 shown in FIG. 2. Further, the volume and intensity of sound generated and broadcast through speakers may be adjusted via the same activity control by defining control regions for the activity control.

Figure 5C:
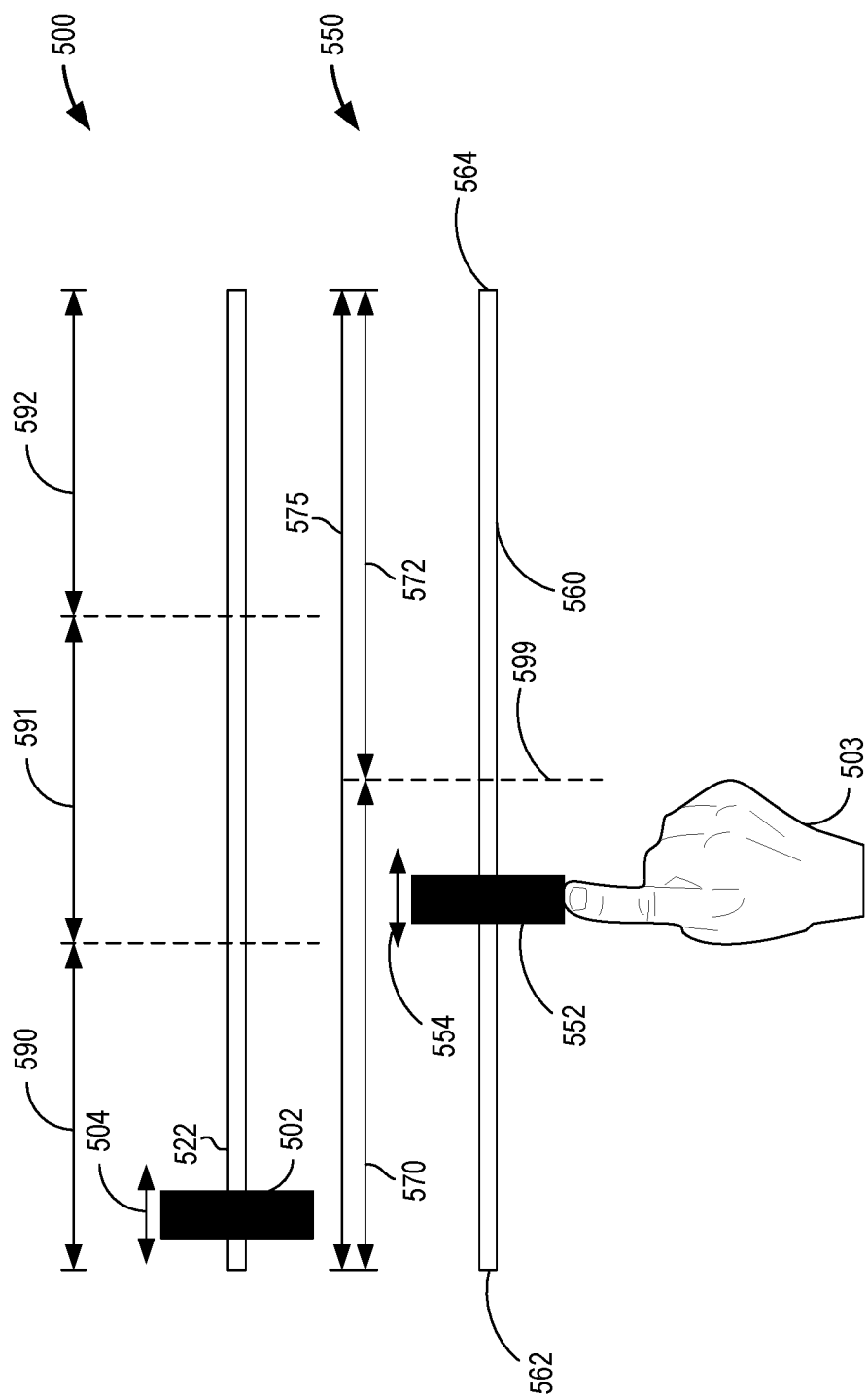
FIG. 5C shows a schematic depiction of two activity controls with example control regions.
Figure 6:
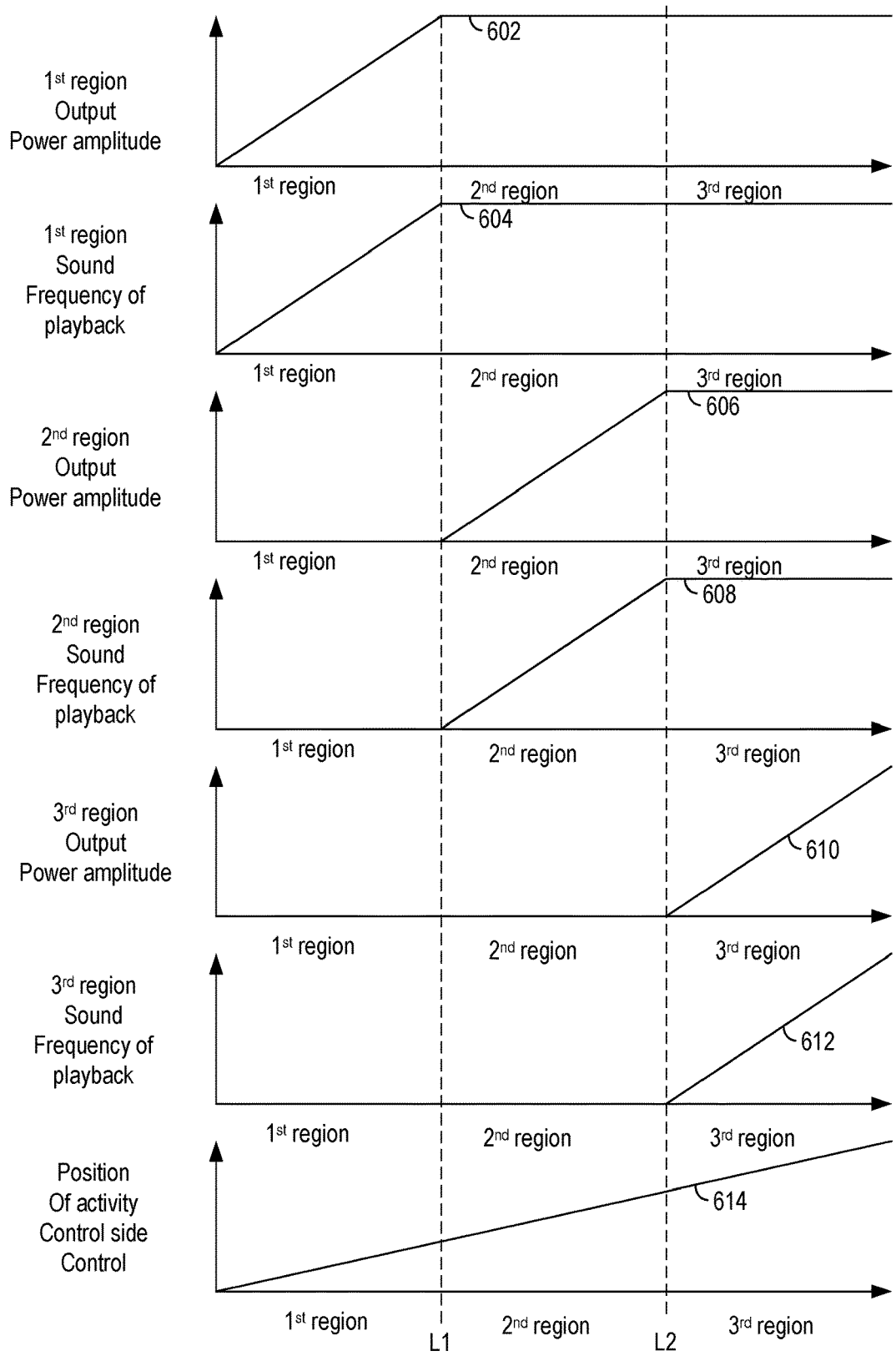
FIG. 6 shows plots of audio attributes that may be modified according to a state of the user interface shown in FIGS. 5A-5C.

Referring now to FIG. 5C, an example where two activity controls are included in the system of FIGS. 1-3 is shown. Activity control 500 is the same activity control that is shown in FIGS. 5A and 5B. Further, activity control 500 includes the same previously mentioned control regions 590-592. Activity control 500 also includes the same slide bar 502 and slide bar guide 522. Activity control 500 may operate and provide the functionality previously described.

Second activity control 550 includes a slide bar 552 and a slide bar guide 560. The slide bar 552 may be moved longitudinally left and right along slide bar guide 560 and between left extent 562 and right extent 564 as indicated by arrows 554 via user 503. In this example, second activity control 550 has a control range or range of authority 575 that is subdivided into two control regions 570 and 572, although range of authority 575 may be subdivided into additional control regions if desired. In one example, surround sound control parameters may be adjusted as a function of a position of slide bar 552 and the control region in which slide bar 552 is located. For example, when slide bar 552 is positioned in first control region 570 a center spread may be increased as slide bar 552 is moved from extent 562 toward vertical line 599. Increasing the center spread may change sound distribution from a center speaker to front left and right speakers. The center spread may reach a maximum level when slide bar 552 reaches the position of vertical line 599. If slide bar moves into second control region 572, then the level of up-mixed channels may be adjusted. For example, the level of up-mixed channels may increase as slide bar 552 moves from vertical line 599 to extent 564. Second activity control 550 may also adjust other surround sound control parameters such as room size emulation, delay time, and dynamic compression. Further, second activity control 550 may adjust sound control parameters for vehicle specific sound control parameters. For example, second activity control 550 may adjust delivery of sound elements to speakers to enhance sound reception for a particular passenger (e.g., front driver, front passenger, etc.).

In an example, the second activity control 550 may adjust the location of specific sound to different regions of the vehicle. For example, the second activity control may adjust the sound distribution and/or location within the various vehicle zones (e.g., front left passenger, front right passenger, etc.) differently for the different sound group regions, such as steady-state sound elements, dynamic sound elements, and/or surreal sound elements. The user input controls may thus provide for adjustment of the vehicle zone to provide different control of each of the different group regions in each of the vehicle zones. In another example, the user input controls may provide for movement from one region to another of only one of the group regions, such as the steady-state sound element.

Thus, activity controls may be assigned to adjust more than one sound control parameter. Further, two or more activity controls may be provided to further increase system flexibility and user experience. In this way, a single activity control may be assigned one or more functions to reduce a number of user inputs, thereby reducing system complexity as perceived by a user.

Further, FIG. 6 shows a relationship between audio attributes of sound elements and a position of an activity control other user interface while operating in the manual mode of the naturescape feature. The plots show how the in-vehicle computing system 109 shown in FIG. 1 or an audio system 232 shown in FIG. 2 may adjust sound elements according to the method of FIGS. 7A and 7B, and the system of FIGS. 1-3.

The first plot from the top of FIG. 6 is a plot of sound output power amplitude or volume versus activity control regions (e.g., 590-592). The vertical axis represents the sound output power amplitude for sound elements that are included in a first group (e.g., steady-state sound elements) of sound elements that are associated with a first control region of the activity control. The sound output power amplitude increases in the direction of the vertical axis arrow. The horizontal axis represents activity control regions and it is broken into three regions as shown in FIG. 5B. Trace 602 represents the sound output power amplitude or volume for sound elements included in the first group of sound elements.

The second plot from the top of FIG. 6 is a plot of sound frequency of playback (e.g., the frequency a sound is repeated when broadcast via speakers) for sound elements that are included in the first group of sound elements versus activity control regions. The vertical axis represents the frequency of playback for sound elements that are included in a first group of sound elements that are associated with a first control region of the activity control. The horizontal axis represents activity control regions and it is broken into three regions as shown in FIG. 5B. Trace 604 represents the sound frequency of playback for sound elements included in the first group of sound elements.

The third plot from the top of FIG. 6 is a plot of sound output power amplitude or volume versus activity control regions. The vertical axis represents the sound output power amplitude for sound elements that are included in a second group (e.g., dynamic sound elements) of sound elements that are associated with a second control region of the activity control. The sound output power amplitude increases in the direction of the vertical axis arrow. The horizontal axis represents activity control regions and it is broken into three regions as shown in FIG. 5B. Trace 606 represents the sound output power amplitude or volume for sound elements included in the second group of sound elements.

The fourth plot from the top of FIG. 6 is a plot of sound frequency of playback for sound elements that are included in the second group of sound elements versus activity control regions. The vertical axis represents the frequency of playback for sound elements that are included in a second group of sound elements that are associated with a second control region of the activity control. The horizontal axis represents activity control regions and it is broken into three regions as shown in FIG. 5B. Trace 608 represents the sound frequency of playback for sound elements included in the second group of sound elements.

The fifth plot from the top of FIG. 6 is a plot of sound output power amplitude or volume versus activity control regions. The vertical axis represents the sound output power amplitude for sound elements that are included in a third group (e.g., surreal sound elements) of sound elements that are associated with a third control region of the activity control. The sound output power amplitude increases in the direction of the vertical axis arrow. The horizontal axis represents activity control regions and it is broken into three regions as shown in FIG. 5B. Trace 610 represents the sound output power amplitude or volume for sound elements included in the third group of sound elements.

The sixth plot from the top of FIG. 6 is a plot of sound frequency of playback for sound elements that are included in the third group of sound elements versus activity control regions. The vertical axis represents the frequency of playback for sound elements that are included in a third group of sound elements that are associated with a third control region of the activity control. The horizontal axis represents activity control regions and it is broken into three regions as shown in FIG. 5B. Trace 612 represents the sound frequency of playback for sound elements included in the third group of sound elements.

The seventh plot from the top of FIG. 6 is a plot of activity control state or position versus activity control regions. The vertical axis represents the state or position of the activity control (e.g., slide bar 502) and the activity control moves from left to right in the direction of the vertical axis arrow. The horizontal axis represents activity control regions and it is broken into three regions as shown in FIG. 5B. Trace 614 represents the activity control state or position.

At the left most side of the plots, the activity control is positioned at a first extent (e.g., 520 of FIG. 5A and FIG. 5B) of the activity control. The activity control is in the first control region so the sound output power amplitudes or volumes and the sound frequency of playback for sound elements that are included in the second and third groups of sound elements are zero. The sound output power amplitude of sound elements included in the first group of sound elements increases as the position of the activity control moves from the left side of the plot to the right side of the plot. Likewise, the frequency of playback or repetition for sound elements that are included in the first group of sound elements increases as the activity control moves from the left side of the plot to the right side of the plot. The sound output power amplitude of sound elements included in the first group of sound elements ceases increasing when the activity control reaches the position of vertical line L1. Likewise, the frequency of playback or repetition for sound elements that are included in the first group of sound elements ceases increasing when the activity control reaches the position of vertical line L1.

Continuing to move from left to right in the plots, the sound output power amplitude and the frequency of playback for sound elements included in the first group remain constant. The sound output power amplitude of sound elements included in the second group of sound elements increase as the position of the activity control moves from the position of vertical line L1 to vertical line L2. Likewise, the frequency of playback or repetition for sound elements included in the second group of sound elements increase as the activity control moves from the position of vertical line L1 to vertical line L2. The sound output power amplitude and the frequency of playback for sound elements included in the third group remain zero. The sound output power amplitude of sound elements included in the second group of sound elements ceases increasing when the activity control reaches the position of vertical line L2. Likewise, the frequency of playback or repetition for sound elements that are included in the second group of sound elements ceases increasing when the activity control reaches the position of vertical line L2.

After the sound activity control reaches the position of line L2, the sound output power amplitude and the frequency of playback for sound elements included in the first and second groups remain constant. The sound output power amplitude of sound elements included in the third group of sound elements increases as the position of the activity control moves from the position of vertical line L2 to the activity control extent (e.g., 524 of FIG. 5A) or end of travel. Likewise, the frequency of playback or repetition for sound elements that are included in the third group of sound elements increase as the activity control moves from the position of vertical line L2 to the activity control extent (e.g., 524 of FIG. 5A) or end of travel.

In this way, natural sounds may be provided to a user via the naturescape feature, in one of the manual mode and the automated mode. As elaborated above, the automated mode may automatically monitor vehicle conditions, such as vehicle location, environmental changes, and a user emotional state, and may provide sound elements to the user. Based on the state of the vehicle, an audio system may provide sound elements. Some sound elements may be based on actual sounds detected outside the vehicle (e.g., real sound elements), while other sound elements may not be detected outside the vehicle (e.g., synthetic sound elements). Further, in the manual mode, a user may select a desired natural scene, and may adjust a mix of corresponding sound elements according to user preference. By providing natural sounds to a vehicle user, a more immersive sonic experience may be created, decreasing user stress and increasing customer satisfaction.

Figure 7A:
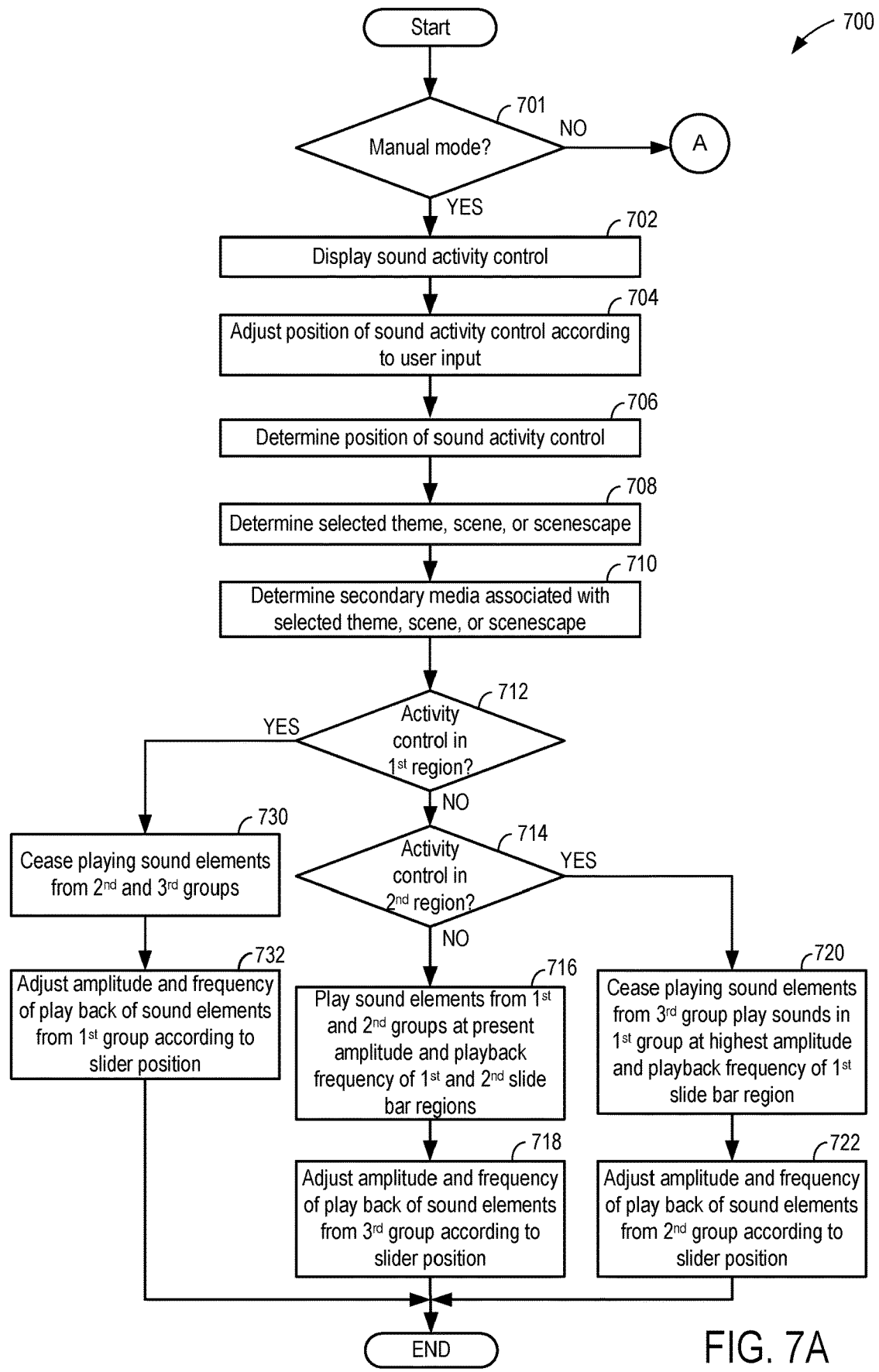
FIGS. 7A and 7B show a flow chart of an example method for generating sound via an audio or infotainment system.
Figure 7B:
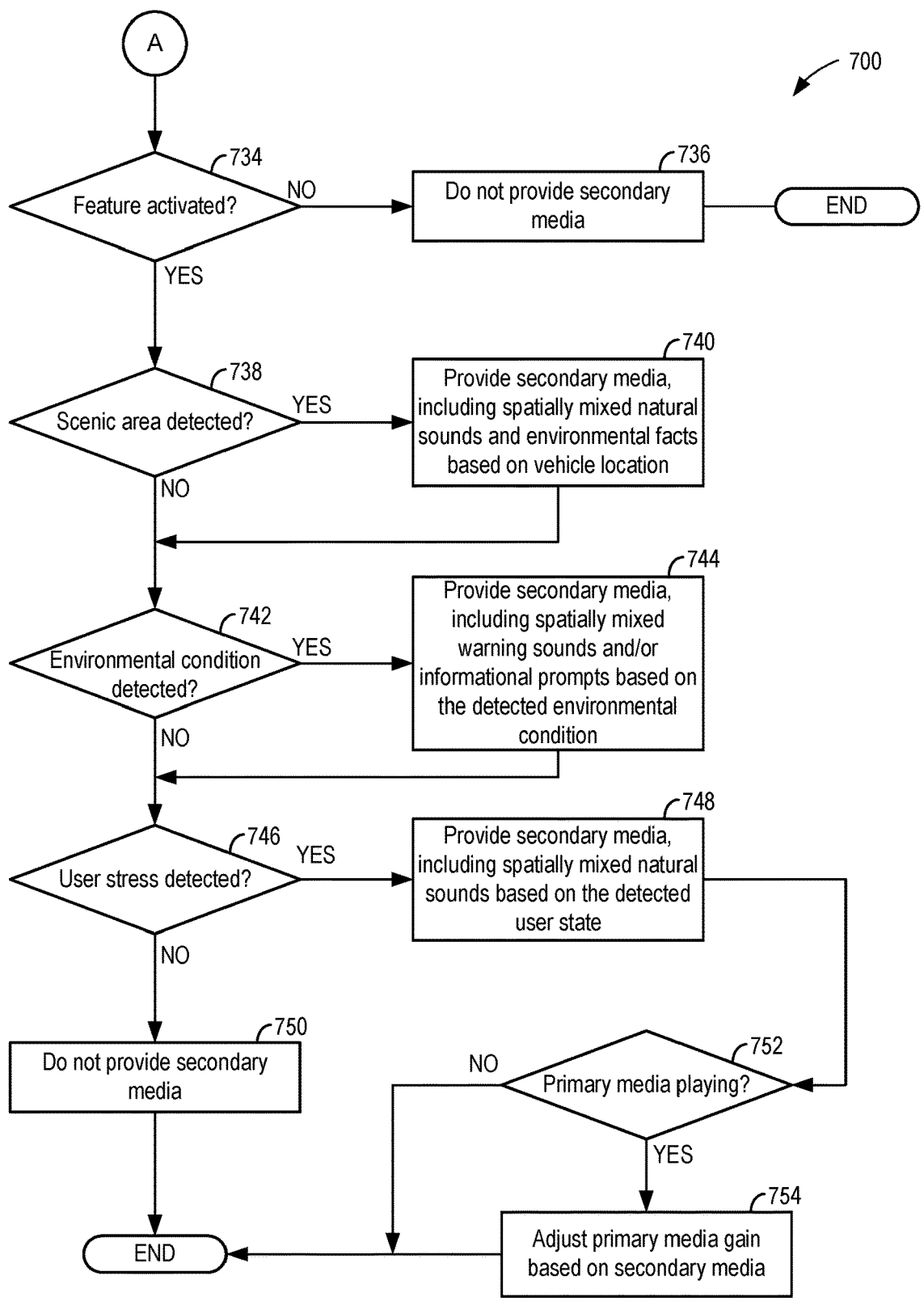
Figure 8:
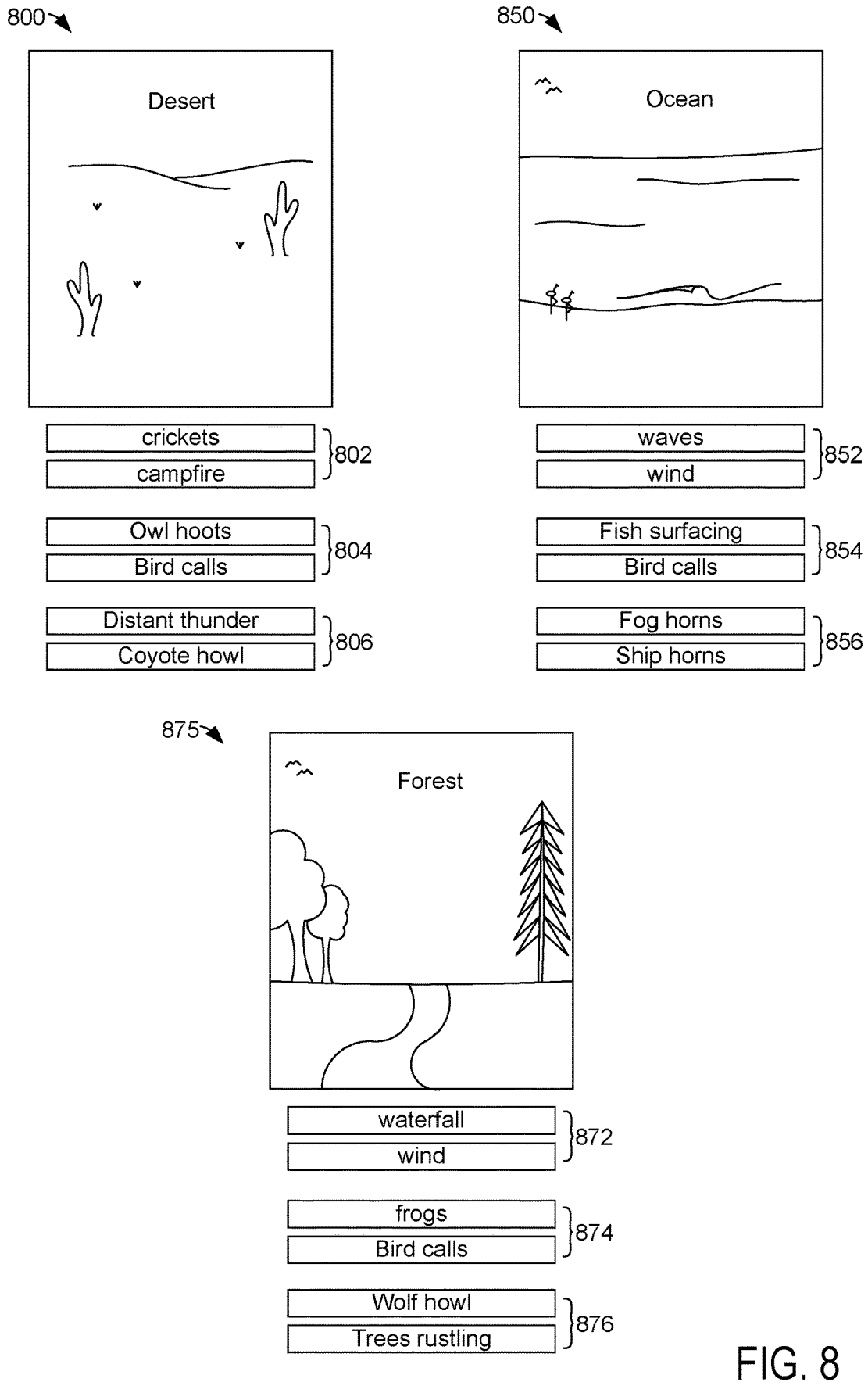
FIG. 8 shows example scenes and sound elements associated with the scenes.

Therefore, FIGS. 7A and 7B show a flow chart for an example method 700 for adjusting audio output (e.g., in a vehicle) to provide a sound environment via a naturescape feature, the naturescape feature including an automated mode and a manual mode. For example, secondary media (e.g., natural sounds) may be provided in addition to primary media (e.g., music, talk radio, voice calls, and the like) in order to increase customer satisfaction. In particular, method 700 is described with respect to the in-vehicle entertainment system of FIGS. 1 and 2, including in-vehicle computing system 109. However, in other examples, method 700 may be carried out by other computing systems. Further method 700 is described with respect to the audio system of FIG. 3. Instructions for carrying out method 700 may be stored in non-transitory memory of the in-vehicle computing system (e.g., storage device 208 shown in FIG. 2) based on the stored instructions and in conjunction with signals received from sensors of the vehicle system such as the sensors described hereinabove with reference to FIGS. 2 and 3.

At 701, method 700 includes determining whether the in-vehicle computing system is configured to provide sound elements via the manual mode or the automated mode. In some examples, a user may adjust a setting in order to select between the manual mode and the automated mode. In other examples, in-vehicle computing system may automatically transition between the manual mode and the automated mode based on vehicle operating conditions. Further still, the mode may be a pre-set condition, and a vehicle may be configured to operate exclusively in one of the manual mode and the automated mode.

If the controller determines that the in-vehicle computing system is operating in the manual mode at 701 ("YES"), method 700 proceeds to 702 and includes receiving data from a touch screen display to determine if a user is touching the display to indicate a desired state or position for the one or more sound activity controls. Method 700 determines if a user is attempting to adjust a position of the sound activity controls (e.g., slider bar 502 shown in FIG. 5A) and updates the position of the sound activity control at 704 if it is determined that the user is attempting to adjust the position of the sound activity control.

At 706, method 700 determines the state or position of the sound activity control according to data received from the touch screen display or other user input device. Method 700 may also subdivide the control range of the sound activity control into a plurality of control regions as shown in FIG. 5B. For example, the control range of the sound activity control may be subdivided based on the actual total number of groups of sound elements (e.g., a first group of sound elements may be steady-state sound elements; a second group of sound elements may be dynamic sound elements; a third group of sound elements may be surreal sound elements) and physical dimensions of the sound activity control. Thus, if there are three sound element groups, the range of the sound activity control may be subdivided into three equal length control regions as shown in FIG. 5B. In other examples, the control regions may be a function of or based on surround sound control parameters or other sound control parameters. Method 700 may determine the state or position of the sound activity control and in which region of control the sound activity control is positioned according to data output via the touch panel display or other device. Method 700 proceeds to 708.

At 708, method 700 determines a theme, scene, or environment via receiving a selection from a user input device (e.g., a touch screen display). The theme, scene, or environment selections may include but are not limited to a desert, rain forest, sea shore, etc. Further, a theme may be more abstract, such as a theme with sound elements selected to reduce anxiety. In addition, in some examples, two or more themes, scenes, or environments may be selected so that sound elements from different themes, scenes, or environments may be combined, if desired. Method 700 proceeds to 710.

At 710, method 700 determines sound elements that are associated with the selected theme, scene, or environment. The sound elements for the selected theme, scene, or environment may also be grouped. For example, a desert theme may include sound elements of crickets included in a first group (e.g., steady-state) of sound elements that also includes sound elements of a light desert wind and/or sound elements of a campfire. The desert theme may also include bird calls in a second group (e.g., dynamic) of sound elements that also includes sound elements of distant thunder. In addition, the desert theme may include coyote howling in a third group (e.g., surreal) of sound elements that also includes sound of a distant train whistle. Thus, each theme, scene, or environment may be associated with one or more groups of sound elements, and the one or more groups of sound elements may be further differentiated by sound element classification (e.g., steady-state, dynamic, and surreal). The sound elements may be retrieved from non-volatile memory when a theme, scene, or environment is selected. In addition, a visual representation of the selected theme, scene, or environment may be displayed via the in-vehicle computing system. Further, in some examples, the sound elements may be retrieved from a remote server via a wireless connection. Method 700 proceeds to 712.

At 712, method 700 determines if the sound activity control is positioned within a first control region according to output of a user input device. If method 700 determines that the sound activity control is within a first control region ("YES"), method 700 proceeds to 730.

If method 700 determines that the sound activity control is not within the first control region ("NO"), method 700 proceeds to 714. At 714, method 700 determines if the sound activity control is positioned within a second control region according to output of a user input device. If method 700 determines that the sound activity control is within a second control region ("YES"), method 700 proceeds to 720.

If method 700 determines that the sound activity control is not within the second control region ("NO"), method 700 proceeds to 716. It should be noted that although method 700 includes provisions for three control regions, the actual total number of control regions may be increased or decreased in a similar way. Additional groups of sound elements may be added by increasing the number of control regions.

At 730, method 700 ceases playing back or broadcasting sound elements from the second and third groups of sound elements. Further, method 700 adjusts a sound output power of sound elements that are included in the second and third groups of sound elements to zero. Method 700 also adjusts the frequency of playback or repetition of sound elements that are included in the second and third groups of sound elements to a base rate (e.g., a slowest frequency that the sound elements may be played back or broadcast via speakers). Thus, if the sound activity control is moved from a second control region to a first control region as may occur by moving slider bar 402 of FIG. 5B from right to left, sound elements included in the second and third groups of sound elements are not played back or broadcast via speakers.

At 732, method 700 plays (e.g., broadcasts via speakers) and adjusts volume or sound output power amplitudes and frequency of playback or repetition of sound elements that are included in the first group of sound elements (e.g., steady-state sound elements) associated with the selected theme, scene, or environment. The sound output power amplitude may be adjusted proportionately with a position of the activity control while the activity control is position within the first control region. For example, if the activity control is moved from left to right, the sound power amplitude or volume may increase proportionately with the adjustment of the activity control. Likewise, the frequency of playback or repetition of sound elements that are included in the first group of sound elements may be adjusted proportionately with the position of the activity control while the activity control is positioned within the first control region. For example, if the activity control is moved from left to right, repetition of a recording of sound elements may increase proportionately with the adjustment of the activity control. One example of controlling sound elements of a first group of sound elements in this way is shown in the first and second plots from the top of FIG. 6 between the vertical axis and vertical line L1.

Further, the activity control may be configured to make other sound and/or sound system adjustments according to the control regions of the activity control beyond volume and frequency of repetition adjustments. For example, instead of adjusting the sound output power amplitude and frequency of repetition for sound elements of a first group of sound elements that are associated with the selected theme, scene, or environment, the sound elements of the first group of sound elements may be adjusted in other ways, including but not limited to adjusting the sound elements according to surround sound up-mixer tuning parameters, delay time, reverberation, recreated or emulated sound venues (e.g., hall, stadium, theater, etc.), simulated distance to source of sound, and zonal sound control locations within a vehicle passenger cabin. As one example, adjusting the activity control position may move vehicle occupant's sound perception of listening to crickets chirp in the distance to listening right next to chirping crickets. In addition, where two or more activity controls are implemented or realized at once in the vehicle or by the in-vehicle computing system 109, one activity control may adjust sound elements being played back, volume of sound elements being played back, and frequency or repetition of sound elements being played back. The other activity control may adjust surround sound up-mixer tuning parameters and zonal sound control within a vehicle. Method 700 proceeds to exit.

At 712, method 700 maintains playing sound elements in the first group and in the second group at their present sound output power levels. Method 700 also maintains repetition rates of sound elements in the first and second groups at their present frequency or rate. Thus, if the sound activity control is moved from a second control region to a third control region as may occur by moving slider bar 502 of FIG. 5B from right to left, sound elements included in the first and second groups continue to be played back or broadcast via speakers as they were just before entering the third control region. Method 700 proceeds to 714.

At 714, method 700 adjusts volume or sound output power amplitudes and frequency of playback or repetition of sound elements that are included in the third group of sound elements (e.g., surreal sound elements) associated with the selected theme, scene, or environment. The sound output power amplitude may be adjusted proportionately with a position of the activity control while the activity control is position within the third control region. Likewise, the frequency of playback or repetition of sound elements that are included in the third group of sound elements may be adjusted proportionately with the position of the activity control while the activity control is positioned within the third control region.

One example of controlling sound elements of a third group of sound elements in this way is shown in the fifth and sixth plots from the top of FIG. 6 between vertical line L2 and the right limit of the plots. As previously mentioned, the activity control may be configured to make other sound and/or sound system adjustments according to the control regions of the activity control beyond volume and frequency of repetition adjustments. As one example, adjusting the activity control may move vehicle occupant's sound perception of listening to a coyote howling in the distance to listening right next to a howling coyote. In addition, where two or more activity controls are implemented or realized at once in the vehicle or by the in-vehicle computing system 109, one activity control may adjust sound elements being played back, volume of sound elements being played back, and frequency or repetition of sound elements being played back. The other activity control may adjust surround sound up-mixer tuning parameters and zonal sound control within a vehicle. Method 700 may then end.

At 720, method 700 ceases playing back sound elements that belong to the third group of sound elements and maintains playing sound elements in the first group and in the second group at their present sound output power levels. Method 700 also maintains repetition rates of sound elements in the first group at their present frequency or rate. Thus, if the sound activity control is moved from a first control region to a second control region, or from a third control region to the second control region, sound elements included in the first group of sound elements continue to be played back or broadcast via speakers as they were just before entering the second control region. Method 700 proceeds to 722.

At 722, method 700 adjusts volume or sound output power amplitudes and frequency of playback or repetition of sound elements that are included in the second group of sound elements (e.g., dynamic sound elements) associated with the selected theme, scene, or environment. The sound output power amplitude may be adjusted proportionately with a position of the activity control while the activity control is position within the second control region. Likewise, the frequency of playback or repetition of sound elements that are included in the second group of sound elements may be adjusted proportionately with the position of the activity control while the activity control is positioned within the second control region. One example of controlling sound elements of a second group of sound elements in this way is shown in the third and fourth plots from the top of FIG. 5 between vertical line L1 and vertical line L2.

As previously mentioned, the activity control may be configured to make other sound and/or sound system adjustments according to the control regions of the activity control beyond volume and frequency of repetition adjustments. As one example, adjusting the activity control may move vehicle occupant's sound perception of listening to a bird calling in the distance to listening right next to a bird that is calling. In addition, where two or more activity controls are implemented or realized at once in the vehicle or by the in-vehicle computing system 109, one activity control may adjust sound elements being played back, volume of sound elements being played back, and frequency or repetition of sound elements being played back. The other activity control may adjust surround sound up-mixer tuning parameters and zonal sound control within a vehicle. Method 700 may then end.

If instead method 700 determines that the in-vehicle computing system is configured to provide sound elements in the automated mode at 701, method 700 proceeds to 734 and includes determining whether the naturescape feature is activated. For example, the naturescape feature may be deactivated based on a user input, so that secondary media (e.g., natural sound elements) are not provided based on operating conditions and/or a position of the activity control.

If method 700 determines that the naturescape feature is not activated at 734 ("NO"), method 700 continues to 736 and includes not providing secondary media. For example, the controller may not select sound elements corresponding to an environment, and may not reproduce the sound elements via the audio system. Further, the controller may not adjust a main system audio (e.g., primary media) based on the secondary media. Method 700 may then end.

If method 700 determines that the naturescape feature is activated at 734 ("YES"), method 700 continues to 738 and includes determining whether a scenic area is detected. For example, method 700 may determine whether the vehicle is in a scenic area based in part on a GPS signal from a GPS sensor (e.g., such as GPS sensor of sensor subsystem 210). As an example, method 700 may compare a vehicle location (e.g., determined based on the GPS signal) to a database of scenic areas, such as parks, beaches, and the like. The database of scenic areas may be stored in controller memory, or may be stored in a remote location and accessed via a wireless connection. Further, the scenic area may be detected by one or more vehicle sensors. As an example, a microphone may be coupled to an exterior of the vehicle (e.g., such as microphone 374 of FIG. 3), and may monitor external sounds. For example, the processor may include an algorithm for analyzing an audio signal from the microphone in order to detect scenic natural environments. For example, a presence of natural sounds such as wildlife sounds, and an absence of urban sounds, such as traffic, may be used to determine that the vehicle is in a scenic area. Further, in some examples, a user may indicate that the vehicle is in a scenic area via an input, such as a button press via a touchscreen.

If method 700 determines that a scenic area is detected at 738 ("YES"), method 700 proceeds to 740 and includes providing secondary media, including spatially mixed sound elements, such as natural sounds and environmental facts based on the vehicle location. As elaborated with respect to FIG. 4, the secondary media for a scenic area may comprise several sound elements, such as ambient natural sounds (e.g., such as rain and ocean waves), spatially mixed natural sounds (e.g., such as wildlife sounds and other directional natural sounds), and information regarding the scenic area. Spatial mixing may be used to place sound elements in a virtual sound space, so that each sound element has a perceived location. Further, method 700 may refer to a database of facts relating to the scenic area, and may provide these facts to the user via one or both of a visual interface and an audio interface. Method 700 may proceed to 742.

If method 700 determines that a scenic area is not detected at 738 ("NO"), method 700 proceeds to 742 and includes determining whether an environmental condition is detected, such as a change in the environmental condition. For example, method 700 may monitor for weather changes, such as an incoming storm, rain, a heat wave, and the like. For example, the in-vehicle computing system may be communicatively coupled to one or more remote servers via a wireless network, and may receive data from a weather database regarding weather conditions at the vehicle location. Further, the in-vehicle computing system may monitor nearby weather conditions in order to predict upcoming changes in the environmental condition. As another example, sensors of the vehicle may be used to monitor for environmental changes. As an example, the vehicle may be equipped with sensors including a barometer and a thermometer, and may predict environmental changes based on signal from the barometer and the thermometer. For example, a sudden drop in pressure, as measured by the barometer, may indicate an upcoming environmental change. Similarly, a sudden increase in temperature may indicate an upcoming environmental change. As yet another example, the in-vehicle computing system may receive environmental alerts from a proprietary external service, the proprietary external service including an application monitoring for environmental changes based on weather data, traffic data, news, and the like. In response to such an environmental alert, method 700 may determine that an environmental condition is detected.

If method 700 determines that an environmental condition is detected ("YES"), method 700 continues to 744 and includes providing secondary media, including spatially mixed warning sounds and/or informational prompts based on the detected environmental condition. For example, method 700 may play sounds relating to the sensed environmental condition. As a first example, in response to an approaching storm, method 700 may play sound elements corresponding to thunder and spatially mixed to be perceived as originating in the direction of the storm. Further, method 700 may play sound elements representing rain, and may incorporate other media (e.g., such as lights) in order to indicate the environmental condition. In addition to these environmental sound elements, method 700 may provide one or more of a warning sound, a warning message, and an informational prompt relating to the environmental condition. For example, in response to an environmental condition, a distinctive warning sound may play, followed by an informational message describing the environmental condition and providing potential resources to the user. As an example, in response to a storm, method 700 may inform a user of the storm location and intensity, and may direct a user to a rest location in order to avoid the storm. In some examples, secondary media relating to an environmental condition may be layered over secondary media relating to a scenic area (e.g., such as provided at 740). In other examples, secondary media relating to the scenic area may be muted in response to the environmental condition. Method 700 may then proceed to 746.

If method 700 instead determines that an environmental condition is not detected ("NO"), method 700 continues to 746 and includes determining whether user stress is detected. For example, method 700 may monitor an emotional state of a user (or of a plurality of users) via a variety of methods. As a first example, method 700 may infer an emotional state of the user based on vehicle conditions. For example, method 700 may detect heavy traffic (e.g., via a navigational subsystem such as navigational subsystem 211 of FIG. 2), and may determine that a user emotional state includes stress due to the heavy traffic. For example, if an amount of traffic exceeds a threshold amount of traffic, method 700 may determine that stress is detected. As another example, the external microphone may detect disturbing sounds outside the vehicle, such as heavy urban sounds (e.g., honking, construction, highway noise, crowds, and the like), and may infer that the user emotional state includes stress due to the disturbing sounds. For example, if the external sounds exceed a threshold noise, method 700 may infer that stress is detected. As yet another example, the vehicle sensors may include biometric sensors. For example, the vehicle may include one or more of an infrared camera for monitoring a user temperature, a heartrate monitor coupled to the steering wheel for monitoring a heartrate, a camera configured to monitor facial expressions, and a microphone for monitoring a user breathing rate. Further, a user's wearable device (e.g., such a smart watch) may be communicatively coupled to the in-vehicle computing system, and may provide biometric data. Based on biometric data (e.g., collected by the vehicle sensors and/or a wearable device), method 700 may monitor the user's emotional state for high levels of stress. For example, if a user's heartrate exceeds a threshold heartrate, method 700 may determine that stress is detected. As another example, if a user's facial expressions, as monitored by a camera, are judged as displeased, method 700 may determine that stress is detected.

If method 700 determines that user stress is not detected at 746 ("NO"), method 700 proceeds to 750 and includes not providing secondary media. For example, additional sound elements may not be provided in order to create an immersive sound environment. Method 700 may then end.

If method 700 instead determines that user stress is detected at 746 ("YES"), method 700 continues to 748 and includes providing secondary media, including spatially mixed natural sounds based on the detected user emotional state. For example, while the secondary media corresponding to a scenic area and the secondary media corresponding to an environmental condition are configured to incorporate elements of the external environment in the sound environment of the vehicle, the opposite may be desired in response to user stress. In particular, the vehicle environment may be an active stressor for the user (e.g., due to traffic, noise, and the like), and secondary media may be provided in order to decrease user stress by minimizing the impact of the external environment. For example, although the external sound environment (e.g., outside the vehicle) may include traffic sounds, construction sounds, and the like, secondary media may be provided so that the interior sound environment includes elements of a peaceful natural scene, such as a secluded forest. The type of natural sounds provided in response to user stress may be pre-determined, or may be selected by a user upon activating the naturescape feature. Further, while providing natural sound elements in response to user stress, the user's emotional state may be continuously monitored to ensure that the selected sounds are having the intended effect of reducing user stress. For example, if method 700 determines that user stress is not decreasing, or is increasing, method 700 may transition to providing different sound elements. As an example, the peaceful forest may not reduce user stress, so method 700 may instead provide sound elements corresponding to a tropical beach, such as ocean waves, seagulls, palm tree leaves blowing in the wind, and the like.

At 752, method 700 determines whether primary media is playing. For example, the primary media may be an audio stream playing via the main system audio, such as music, talk radio, a podcast, a voice call, audio from a motion picture, and the like.

If method 700 determines that primary media is playing at 752, method 700 proceeds to 754 and includes adjusting audio settings, such as the primary media gain, based on the secondary media. For example, while providing secondary media (e.g., such as natural sounds and informational facts), the primary media gain may be lowered so that the secondary media is audible. Based on the type of secondary media and the type of primary media, settings may be adjusted differently. As an example, the secondary media may be muted or ducked in response to a voice call, and may not be adjusted during talk radio or movie audio. Method 700 may then end.

If method 700 instead determines that primary media is not playing at 752 ("NO"), method 700 may end.

In this way, the naturescape feature may be used in one of the manual mode and the automated mode in order to provide immersive sound environments in a motor vehicle. For example, in the manual mode, a user may select a desired natural scene, and the audio system of the motor vehicle may provide sound elements corresponding to the natural scene, the sound elements spatially mixed to be perceived as spatially located. Further, in the automated mode, a controller (e.g., such as an in-vehicle computing system) may monitor for a variety of conditions, including the presence of the vehicle in a scenic location, an environmental change (e.g., such as a weather change), and user stress. In response to each of these conditions, the audio system may provide sound elements. For example, in response to a scenic environment, the in-vehicle computing system may select sound elements that bring the external environmental into the vehicle, such as by reproducing and/or imitating natural sounds corresponding to the vehicle location, and providing information regarding the vehicle location. Thus, a user may feel more immersed and connected to the surrounding environment. Similarly, in response to an environmental change, the in-vehicle computing system may select sound elements corresponding to the environmental change, along with warning sounds and verbal alerts, in order to inform the user of the environmental change. By providing sound elements corresponding to the environmental change, elements of the external environment are reproduced inside the vehicle. However, in response to user stress, the opposite effect may be achieved by providing sound elements. For example, the external environment may be stressful, so the in-vehicle computing system may provide sound elements from a remote location in order to decrease the effect of the external environment on the user.

Referring now to FIG. 8, example scenes and their associated sound elements are shown. FIG. 8 shows two example scenes and associated sound elements that may be made available to a user to enhance a user's experience while traveling in a vehicle. In one example, the example scenes may be selected by a user in the manual mode of the naturescape feature. As another example, the in-vehicle computing system may select such example scenes based on a vehicle location corresponding to the example scenes. As yet another example, the in-vehicle computing system may select such example scenes in response to user stress.

An example, desert scene 800 is shown. In one example, a user may wish to experience the sound elements of a desert landscape. The user may select a desert scene and a picture or rendering of a desert may be shown on an in vehicle display screen as shown in FIG. 1 at 111. In another example, the vehicle may be located in a desert environment. The desert scene may include a plurality of associated sound elements 802-806 that are stored in controller non-volatile memory. The associated sound elements may be grouped together according to the type of sound elements or the way the sound elements are applied via the in-vehicle computing system 109 or audio system 232. In this example, a first group of sound elements 802 may be referred to as steady-state elements or sound elements. The steady-state sound elements in this example are sound elements of crickets and sound elements of a campfire. A second group of sound elements 804 may be referred to as dynamic elements or sound elements. The dynamic sound elements in this example are sound elements of owl hoots and sound elements of bird calls. A third group of sound elements may be referred to as surreal elements or sound elements. The surreal sound elements in this example are sound elements of distant thunder and sound elements of a coyote howling. Of course, the sound groups may be referred to in ways other than steady-state, dynamic, and surreal, if desired. The sound elements may be played back or broadcast via speakers as described in the method of FIGS. 7A and 7B.

An example, ocean scene 850 is also shown. A user may wish to experience the sound elements of an ocean front beach. The user may select an ocean scene and a picture or rendering of the ocean may be shown on an in vehicle display screen. As another example, the vehicle is located near a beach. As yet another example, the ocean scene may be selected in response to user stress. The ocean scene may include a plurality of associated sound elements 852-856 that are stored in controller non-volatile memory. The associated sound elements may be grouped together as previously described. In this example, a first group of sound elements 852 may be referred to as steady-state elements or sound elements. The steady-state sound elements in this example are sound elements of waves and sound elements of wind. A second group of sound elements 854 may be referred to as dynamic elements or sound elements. The dynamic sound elements in this example are sound elements of fish surfacing and birds calling. A third group of sound elements may be referred to as surreal elements or sound elements. The surreal sound elements in this example are sound elements of fog horns and ship horns. The sound elements may be played back or broadcast via speakers as described in the method of FIGS. 7A and 7B.

An example, ocean scene 875 is also shown. A user may wish to experience the sound elements of a forest. The user may select a forest scene and a picture or rendering of the ocean may be shown on an in vehicle display screen. As another example, the vehicle is driving through a forest, such as a national park. As yet another example, the forest scene may be selected in response to user stress. The forest scene may include a plurality of associated sound elements 872-876 that are stored in controller non-volatile memory. The associated sound elements may be grouped together as previously described. In this example, a first group of sound elements 872 may be referred to as steady-state elements or sound elements. The steady-state sound elements in this example are sound elements of a waterfall and sound elements of wind. A second group of sound elements 874 may be referred to as dynamic elements or sound elements. The dynamic sound elements in this example are sound elements of frogs and birds calling. A third group of sound elements may be referred to as surreal elements or sound elements. The surreal sound elements in this example are sound elements of wolves howling and trees rustling. The sound elements may be played back or broadcast via speakers as described in the method of FIGS. 7A and 7B.

In this way, an immersive sound environment may be provided to a vehicle user via playing spatially mixed natural sounds. For example, a naturescape feature may include a manual mode and an automated mode. Further, while operating in the automated mode, sound elements may be provided based on one or more states associated with the vehicle (e.g., such as a vehicle location, an environmental condition, and an emotional state of a user). For example, by providing sound elements corresponding to the vehicle location, a user curiosity regarding the location may be increased. Further, sound elements provided by the naturescape feature may be provided via spatial mixing, so that each sound element may be perceived to originate from a distinct spatial location. For example, by providing sounds with spatial mixing, an immersive, surround-sound experience may be provided, which may increase customer satisfaction. Overall, by providing sound elements based on a state associated with the vehicle, user enjoyment may be increased while user stress is decreased.

The technical effect of selecting sound elements based on a state of a vehicle is that the sound elements reproduced via an audio system of a vehicle in response to vehicle conditions, each sound element mapped to a virtual location.

As an example, a method comprises: selecting a sound element, the sound element corresponding to a natural environment; and broadcasting the sound element via one or more speakers of a vehicle. In the preceding example, additionally or optionally, the sound element is selected based on at least one vehicle state of the vehicle. In one or both of the preceding examples, the method additionally or optionally further comprises: adjusting a setting for each of the one or more speakers based on a virtual position of the sound element. In any or all of the preceding examples, additionally or optionally, the at least one vehicle state is at least one of a position of a vehicle, an environmental condition, and an emotional state of a vehicle user. In any or all of the preceding examples, additionally or optionally, selecting the sound element in response to the at least one vehicle state includes, in response to the position of the vehicle being a pre-determined scenic area, selecting the sound element corresponding to a sound outside the vehicle. In any or all of the preceding examples, additionally or optionally, selecting the sound element in response to the at least one vehicle state includes, in response to detecting a change in the environmental condition, selecting the sound element corresponding to a sound outside the vehicle. In any or all of the preceding examples, additionally or optionally, selecting the sound element in response to the at least one vehicle state includes, in response to the emotional state of the vehicle user including stress, selecting the sound element not corresponding to a sound outside the vehicle. In any or all of the preceding examples, additionally or optionally, the position of the vehicle is determined based on a signal from GPS sensor. In any or all of the preceding examples, additionally or optionally, the environmental condition is determined based on a connection with a remote server. In any or all of the preceding examples, additionally or optionally, the emotional state of the vehicle user is determined based on at least one of navigation data, an infrared camera, a heartrate monitor, a camera, a microphone, and a connection with a wearable device. In any or all of the preceding examples, additionally or optionally, the virtual position indexed to the sound element corresponds to a location outside the vehicle, and the virtual position of the sound element is mapped to a virtual speaker region, the virtual speaker region inside the vehicle. In any or all of the preceding examples, additionally or optionally, broadcasting the sound element via the plurality of speakers of the vehicle, the setting for each speaker of the plurality of speakers adjusted based on the virtual position of the sound element includes: adjusting a gain for each speaker of the plurality of speakers based on a mapping between the virtual position of the sound element and a virtual speaker region. In any or all of the preceding examples, additionally or optionally, a gain for a first speaker of a plurality of speakers is higher relative to a gain for a second speaker of the plurality of speakers. In any or all of the preceding examples, additionally or optionally, the gain for each speaker of the plurality of speakers is further adjusted based on a second media source, the second media source including one of a music file, a radio signal, and a movie. In any or all of the preceding examples, additionally or optionally, the sound element is selected based on a sound detected outside the vehicle by a microphone coupled to an exterior of the vehicle.

As another example, a system comprises: a computing system of a vehicle; a plurality of speakers; a plurality of sensors communicatively coupled to the computing system, the plurality of sensors including a GPS sensor; a processor communicatively coupled to the computing system; and a storage device storing instructions executable by the processor to: broadcast a first sound element and a second sound element via the plurality of speakers, both of the first sound element and the second sound element selected based on a signal from the GPS sensor, the first sound element indexed to a first virtual location, and the second sound element indexed to a second virtual location. In the preceding example, additionally or optionally, the storage device contains further instructions executable by the processor to: adjust a first audio signal to each of the plurality of speakers based on the first virtual location of the first sound element; and adjust a second audio signal to each of the plurality of speakers based on the second virtual location of the second sound element. In one or both of the preceding examples, additionally or optionally, the first sound element corresponds to a sound detected outside the vehicle via a microphone coupled to an exterior of the vehicle. In any or all of the preceding examples, additionally or optionally, the second sound element does not correspond to a sound detected outside the vehicle. In any or all of the preceding examples, additionally or optionally, each of the first sound element and the second sound element are selected from a database of sound stored in the storage device.

As another example, a method comprises: generating a sound environment in a vehicle based on a natural environment, the natural environment selected based on a vehicle state, the vehicle state determined based on at least one sensor of a plurality of sensors. In the preceding example, additionally or optionally, the natural environment is proximate to a vehicle location, the vehicle location determined based on a signal from a GPS sensor. In one or both of the preceding examples, additionally or optionally, the natural environment is remote from a vehicle location, the vehicle location determined based on a signal from a GPS sensor. In any or all of the preceding examples, additionally or optionally, generating the sound environment in the vehicle based on the natural environment includes: broadcasting a plurality of sound elements, each sound element of the plurality of sound elements selected based on the vehicle state, and each sound element indexed to a virtual location; and adjusting each speaker of a plurality of speakers based on the virtual location indexed to each sound element of the plurality of sound elements. In any or all of the preceding examples, additionally or optionally, the vehicle state includes at least one of a vehicle location, an environmental condition, and an emotional state of a vehicle user, the vehicle location determined based on a signal from GPS sensor, the environmental condition determined based on a weather data, and the emotional state of the vehicle user determined based on a navigation data.

As still another example, a method comprises: in a first mode, generating sounds in a vehicle that match natural sounds determined to occur in a surrounding area of a position of the vehicle; and in a second mode, generating sounds in the vehicle that do not match natural sounds determined to occur in the surrounding area of the position of the vehicle, the sounds selected to balance against the determined natural sounds. In the preceding example, additionally or optionally, the first mode is selected in response to one of the vehicle position proximate to a scenic area and an environmental condition. In one or both of the preceding examples, additionally or optionally, the second mode is selected in response to user stress. In any or all of the preceding examples, additionally or optionally, user stress is detected based on one or more of traffic data, an infrared camera, a microphone, a heartrate monitor, and a signal from a wearable device.

As another example, a method comprises: adjusting an amount of augmentation of external environmental sounds in a vehicle with speakers in the vehicle. In the preceding example, additionally or optionally, adjusting the amount of augmentation of external environmental sounds in a vehicle with speakers in the vehicle includes: in a first mode, increasing an amount of augmentation of external environmental sounds; and in a second mode, decreasing an amount of augmentation of external environmental sounds. In one or both of the preceding examples, additionally or optionally, in the first mode, increasing an amount of augmentation of external environmental sounds includes: broadcasting a first pre-recorded audio file matching a sound of the external environment; and broadcasting a second pre-recorded audio file not matching a sound of the external environment. In any or all of the preceding examples, additionally or optionally, in the second mode, decreasing the amount of augmentation of external environmental sounds includes not augmenting external environmental sounds. In any or all of the preceding examples, additionally or optionally, in the second mode, decreasing the amount of augmentation of external environmental sounds includes broadcasting sounds not included in the external environmental sounds. In any or all of the preceding examples, additionally or optionally, in the second mode, decreasing the amount of augmentation of external environmental sounds includes: in response to determining that the external environmental sounds include traffic sounds, broadcasting sounds not included in the external environmental sounds, the sounds not included in the external environmental sounds include both of bird sounds and rain sounds; and in response to a change in a user mood, decreasing a volume of the bird sounds while increasing a volume of the rain sounds. In any or all of the preceding examples, additionally or optionally, in the first mode, increasing the amount of augmentation of external environmental sounds includes: in response to the vehicle position near an ocean beach, selecting pre-recorded sounds including ocean wave sounds, seagull sounds, and rain sounds; indexing the ocean wave sounds to a first virtual position, the seagull sounds to a second virtual position, and the rain sounds to a third virtual position; determining a first set of speaker settings based on the first virtual position, a second set of speaker settings based on the second virtual position, and a third set of speaker settings based on the third virtual position; broadcasting the ocean wave sounds via the speakers with a first set of speaker settings; broadcasting the seagull sounds via the speakers with a second set of speaker settings; and broadcasting the rain sounds via the speakers with a third set of speaker settings.

The description of embodiments has been presented for purposes of illustration and description. Suitable modifications and variations to the embodiments may be performed in light of the above description or may be acquired from practicing the methods. The methods may be performed by executing stored instructions with one or more logic devices (e.g., processors) in combination with one or more additional hardware elements, such as storage devices, memory, image sensors/lens systems, light sensors, hardware network interfaces/antennas, switches, actuators, clock circuits, etc.

The described methods and associated actions may also be performed in various orders in addition to the order described in this application, in parallel, and/or simultaneously. Further, the described methods may be repeatedly performed. The described systems are exemplary in nature, and may include additional elements and/or omit elements. The subject matter of the present disclosure includes all novel and non-obvious combinations and sub-combinations of the various systems and configurations, and other features, functions, and/or properties disclosed.

As used in this application, an element or step recited in the singular and proceeded with the word "a" or "an" should be understood as not excluding plural of said elements or steps, unless such exclusion is stated. Furthermore, references to "one embodiment" or "one example" of the present disclosure are not intended to be interpreted as excluding the existence of additional embodiments that also incorporate the recited features. The terms "first," "second," and "third," etc. are used merely as labels, and are not intended to impose numerical requirements or a particular positional order on their objects. The following claims particularly point out subject matter from the above disclosure that is regarded as novel and non-obvious.

The invention claimed is:

1. A method, comprising:
   selecting a sound element based on a sound detected outside the vehicle by a microphone coupled to an exterior of the vehicle and based on an emotional state of a vehicle user, the sound element corresponding to a natural environment;
   adjusting a setting for each of one or more speakers of a vehicle based on a virtual position of the sound element corresponding to a location outside the vehicle; and
   broadcasting the sound element via the one or more speakers.

2. The method of claim 1, wherein the sound element is selected based on at least one vehicle state of the vehicle, wherein the at least one vehicle state includes at least one of a position of the vehicle, an environmental condition, and the emotional state of a vehicle user.

3. The method of claim 2, wherein selecting the sound element in response to the at least one vehicle state includes, in response to the position of the vehicle being a predetermined scenic area, selecting the sound element corresponding to a sound outside the vehicle.

4. The method of claim 2, wherein selecting the sound element in response to the at least one vehicle state includes, in response to detecting a change in the environmental condition, selecting the sound element corresponding to a sound outside the vehicle.

5. The method of claim 2, wherein selecting the sound element in response to the at least one vehicle state includes, in response to the emotional state of the vehicle user including stress, selecting the sound element not corresponding to a sound outside the vehicle.

6. The method of claim 2, wherein the emotional state of the vehicle user is determined based on at least one of navigation data, an infrared camera, a heartrate monitor, a camera, a microphone, and a connection with a wearable device.

7. The method of claim 1, wherein the sound element comprises a first pre-recorded audio file matching a sound of the natural environment.

8. The method of claim 1, the virtual position of the sound element is mapped to a virtual speaker region, the virtual speaker region inside the vehicle.

9. The method of claim 1, wherein broadcasting the sound element via the one or more speakers of the vehicle, the setting for each speaker of the one or more speakers adjusted based on the virtual position of the sound element includes:
   adjusting a gain for each speaker of the one or more speakers based on a mapping between the virtual position of the sound element and a virtual speaker region.

10. The method of claim 9, wherein the gain for each speaker of the one or more speakers is further adjusted based on a second media source, the second media source including one of a music file, a radio signal, and a movie.

11. The method of claim 1, further comprising:
    adjusting an additional setting for each of the one or more speakers based on a selection of at least one type of sound element from a group consisting of: steady-state sound elements; dynamic sound elements; and surreal sound elements.

12. The method of claim 1, wherein the adjusting of the additional for each of the one or more speakers based on the selection of the at least one type of sound element is based upon a control region of an activity controller.

13. A system, comprising:
    a computing system of a vehicle;
    a microphone coupled to an exterior of the vehicle;
    a plurality of speakers;
    a plurality of sensors communicatively coupled to the computing system, the plurality of sensors including a GPS sensor;
    a processor communicatively coupled to the computing system; and
    a storage device storing instructions executable by the processor to:
    select at least one of a first sound element and a second sound element based on a sound detected by the microphone and an emotional state of a user of the vehicle, and
    broadcast the first sound element and the second sound element via the plurality of speakers, both of the first sound element and the second sound element selected based on a signal from the GPS sensor, the first sound element indexed to a first virtual location outside the vehicle, and the second sound element indexed to a second virtual location outside the vehicle.

14. The system of claim 13, wherein the storage device contains further instructions executable by the processor to:
    adjust a first audio signal to each of the plurality of speakers based on the first virtual location of the first sound element; and
    adjust a second audio signal to each of the plurality of speakers based on the second virtual location of the second sound element.

15. The system of claim 13, wherein the second sound element does not correspond to a sound detected outside the vehicle.

16. The system of claim 13, where each of the first sound element and the second sound element are selected from a database of sound stored in the storage device.

17. A method, comprising:
    generating a sound environment in a vehicle based on a natural environment, the natural environment selected based on a vehicle state, the vehicle state determined based on at least one sensor of a plurality of sensors, the at least one sensor including an externally-coupled microphone;
    broadcasting a plurality of sound elements, each sound element of the plurality of sound elements selected based on the vehicle state and on an emotional state of a user of the vehicle, and each sound element indexed to a virtual location outside the vehicle; and adjusting each speaker of a plurality of speakers based on the virtual location indexed to each sound element of the plurality of sound elements.

18. The method of claim 17, wherein the natural environment is proximate to a vehicle location, the vehicle location determined based on a signal from a GPS sensor.

19. The method of claim 17, wherein the natural environment is remote from a vehicle location, the vehicle location determined based on a signal from a GPS sensor.

* * * * *